United States Patent
Fang et al.

(10) Patent No.: US 12,011,597 B2
(45) Date of Patent: *Jun. 18, 2024

(54) NERVE CUFF ELECTRODE FOR NEUROMODULATION IN LARGE HUMAN NERVE TRUNKS

(71) Applicant: Neuros Medical, Inc., Aliso Viejo, CA (US)

(72) Inventors: Zi-Ping Fang, Beachwood, OH (US); Nemath Syed Shah, Lyndhurst, OH (US)

(73) Assignee: Neuros Medical, Inc., Aliso Viejo, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/850,843

(22) Filed: Jun. 27, 2022

(65) Prior Publication Data

US 2022/0339446 A1 Oct. 27, 2022

Related U.S. Application Data

(63) Continuation of application No. 17/009,541, filed on Sep. 1, 2020, now Pat. No. 11,413,458, which is a continuation-in-part of application No. 15/510,824, filed as application No. PCT/US2014/055374 on Sep. 12, 2014, now Pat. No. 10,758,723, which is a continuation-in-part of application No. 14/276,200,
(Continued)

(51) Int. Cl.
*A61N 1/36* (2006.01)
*A61N 1/05* (2006.01)

(52) U.S. Cl.
CPC ....... *A61N 1/36071* (2013.01); *A61N 1/0551* (2013.01); *A61N 1/36021* (2013.01); *A61N 1/3616* (2013.01); *A61N 1/36171* (2013.01); *A61N 1/0556* (2013.01)

(58) Field of Classification Search
CPC .............. A61N 1/36071; A61N 1/0551; A61N 1/36021; A61N 1/3616; A61N 1/36171; A61N 1/0556
See application file for complete search history.

(56) References Cited

U.S. PATENT DOCUMENTS

| | | |
|---|---|---|
| 3,738,368 A | 6/1973 | Avery et al. |
| 4,155,366 A | 5/1979 | Di Mucci |
| (Continued) | | |

FOREIGN PATENT DOCUMENTS

| | | |
|---|---|---|
| CN | 102573986 A | 7/2012 |
| DE | 202010015346 U1 | 4/2011 |
| (Continued) | | |

OTHER PUBLICATIONS

Ackermann et al.; Effect of bipolar cuff electrode design on block thresholds in high-frequency electrical neural conduction block; IEEE Transactions on Neural Systems and Rehabilitation Engineering; 17(5); pp. 469-477; Oct. 1, 2009.

(Continued)

*Primary Examiner* — Catherine M Voorhees
*Assistant Examiner* — Roland Dinga
(74) *Attorney, Agent, or Firm* — Shay Glenn LLP

(57) ABSTRACT

A durable nerve cuff electrode for achieving block of an action potential in a large diameter nerve.

20 Claims, 12 Drawing Sheets

Related U.S. Application Data filed on May 13, 2014, now Pat. No. 8,983,612, which is a continuation of application No. 13/474,926, filed on May 18, 2012, now Pat. No. 8,731,676.

(60) Provisional application No. 61/487,877, filed on May 19, 2011.

(56) References Cited

U.S. PATENT DOCUMENTS

| | | |
|---|---|---|
| 4,573,481 A | 3/1986 | Bullara |
| 4,602,624 A | 7/1986 | Naples et al. |
| 4,979,511 A | 12/1990 | Terry |
| 5,143,067 A | 9/1992 | Rise et al. |
| 5,324,322 A | 6/1994 | Grill et al. |
| 5,653,739 A | 8/1997 | Maurer et al. |
| 5,755,750 A | 5/1998 | Petruska et al. |
| 5,964,702 A | 10/1999 | Grill, Jr. et al. |
| 6,058,331 A | 5/2000 | King |
| 6,275,735 B1 | 8/2001 | Jarding et al. |
| 6,292,703 B1 | 9/2001 | Meier et al. |
| 6,456,866 B1 | 9/2002 | Tyler et al. |
| 6,699,275 B1 | 3/2004 | Knudson et al. |
| 6,735,475 B1 | 5/2004 | Whitehurst et al. |
| 6,760,626 B1 | 7/2004 | Boveja |
| 6,836,685 B1 | 12/2004 | Fitz |
| 6,860,851 B2 | 3/2005 | Knudson et al. |
| 6,871,099 B1 | 3/2005 | Whitehurst et al. |
| 7,076,307 B2 | 7/2006 | Boveja et al. |
| 7,167,750 B2 | 1/2007 | Knudson et al. |
| 7,201,757 B2 | 4/2007 | Knudson et al. |
| 7,292,890 B2 | 11/2007 | Whitehurst et al. |
| 7,295,876 B1 | 11/2007 | Erickson |
| 7,302,296 B1 | 11/2007 | Hoffer |
| 7,324,852 B2 | 1/2008 | Barolat et al. |
| 7,389,145 B2 | 6/2008 | Kilgore et al. |
| 7,444,183 B2 | 10/2008 | Knudson et al. |
| 7,463,927 B1 | 12/2008 | Chaouat |
| 7,489,966 B2 | 2/2009 | Leinders et al. |
| 7,555,345 B2 | 6/2009 | Wahlstrand et al. |
| 7,616,990 B2 | 11/2009 | Chavan et al. |
| 7,761,166 B2 | 7/2010 | Giftakis et al. |
| 7,839,415 B2 | 11/2010 | Hillard et al. |
| 7,860,570 B2 | 12/2010 | Whitehurst et al. |
| 7,894,905 B2 | 2/2011 | Pless et al. |
| 7,894,906 B2 | 2/2011 | Shuros |
| 7,979,131 B2 | 7/2011 | Feler et al. |
| 8,027,718 B2 | 9/2011 | Spinner et al. |
| 8,060,208 B2 | 11/2011 | Kilgore et al. |
| 8,060,209 B2 | 11/2011 | Jaax et al. |
| 8,108,052 B2 | 1/2012 | Boling |
| 8,116,882 B2 | 2/2012 | Kowalczewski |
| 8,170,675 B2 | 5/2012 | Alataris et al. |
| 8,185,207 B2 | 5/2012 | Molnar et al. |
| 8,219,202 B2 | 7/2012 | Giftakis et al. |
| 8,224,453 B2 | 7/2012 | De Ridder |
| 8,380,318 B2 | 2/2013 | Kishawi et al. |
| 8,452,417 B2 | 5/2013 | Navarro |
| 8,467,879 B1 | 6/2013 | Whitehurst et al. |
| 8,498,711 B2 | 7/2013 | Roche |
| 8,504,147 B2 | 8/2013 | Deem et al. |
| 8,521,291 B1 | 8/2013 | Cholette et al. |
| 8,560,075 B2 | 10/2013 | Covalin |
| 8,594,796 B2 | 11/2013 | Roche |
| 8,600,505 B2 | 12/2013 | Libbus et al. |
| 8,676,329 B2 | 3/2014 | Wacnik et al. |
| 8,676,331 B2 | 3/2014 | Parker |
| 8,712,547 B2 | 4/2014 | Whitehurst et al. |
| 8,731,676 B2 | 5/2014 | Fang et al. |
| 8,738,140 B2 | 5/2014 | De Ridder |
| 8,755,893 B2 | 6/2014 | Gross et al. |
| 8,761,892 B2 | 6/2014 | Weisgarber et al. |
| 8,788,045 B2 | 7/2014 | Gross et al. |
| 8,805,518 B2 | 8/2014 | King et al. |
| 8,903,502 B2 | 12/2014 | Perryman et al. |
| 8,923,975 B2 | 12/2014 | Bradley |
| 8,965,516 B2 | 2/2015 | Bennett et al. |
| 8,977,362 B2 | 3/2015 | Saab |
| 8,983,612 B2 | 3/2015 | Fang et al. |
| 8,983,614 B2 | 3/2015 | Kilgore et al. |
| 9,031,658 B2 | 5/2015 | Chiao et al. |
| 9,037,248 B2 | 5/2015 | Durand et al. |
| 9,089,700 B2 | 7/2015 | Hlavka et al. |
| 9,095,699 B2 | 8/2015 | Rosenberg et al. |
| 9,132,272 B2 | 9/2015 | Alves et al. |
| 9,259,575 B2 | 2/2016 | Zhao et al. |
| 9,295,840 B1 | 3/2016 | Thacker et al. |
| 9,295,841 B2 | 3/2016 | Fang et al. |
| 9,327,121 B2 | 5/2016 | Thacker et al. |
| 9,339,655 B2 | 5/2016 | Carbunaru |
| 9,387,325 B1 | 7/2016 | Min et al. |
| 9,403,008 B2 | 8/2016 | Howard |
| 9,403,014 B2 | 8/2016 | Kilgore et al. |
| 9,409,019 B2 | 8/2016 | Walker et al. |
| 9,421,372 B2 | 8/2016 | Mashiach et al. |
| 9,604,062 B2 | 3/2017 | Carroll |
| 9,630,011 B2 | 4/2017 | Lipani |
| 9,694,181 B2 | 7/2017 | Bhadra et al. |
| 9,814,881 B2 | 11/2017 | Moffitt |
| 9,884,189 B2 | 2/2018 | Boggs |
| 9,884,192 B2 | 2/2018 | Kilgore et al. |
| 9,889,293 B2 | 2/2018 | Siegel et al. |
| 9,931,510 B2 | 4/2018 | Hou et al. |
| 9,937,348 B1 | 4/2018 | Bradley |
| 9,956,398 B2 | 5/2018 | Callegari et al. |
| 10,086,201 B2 | 10/2018 | Chang et al. |
| 10,105,541 B2 | 10/2018 | Kishawi et al. |
| 10,149,978 B1 | 12/2018 | Park |
| 10,159,838 B2 | 12/2018 | Kim et al. |
| 10,195,434 B2 | 2/2019 | Bhadra et al. |
| 10,238,872 B2 | 3/2019 | Pivonka et al. |
| 10,258,805 B2 | 4/2019 | Reed et al. |
| 10,286,213 B2 | 5/2019 | Fletcher et al. |
| 10,300,273 B2 | 5/2019 | Rooney et al. |
| 10,315,034 B2 | 6/2019 | Hou et al. |
| 10,328,256 B1 | 6/2019 | Gliner |
| 10,390,877 B2 | 8/2019 | Heggeness et al. |
| 10,456,575 B2 | 10/2019 | Kilgore et al. |
| 10,617,870 B2 | 4/2020 | Kilgore et al. |
| 10,632,309 B2 | 4/2020 | McGee et al. |
| 10,675,469 B2 | 6/2020 | Annoni et al. |
| 10,722,703 B2 | 7/2020 | Mitchell |
| 10,758,723 B2 * | 9/2020 | Fang .................. A61N 1/36057 |
| 10,780,270 B2 | 9/2020 | Schepis et al. |
| 10,786,669 B2 | 9/2020 | Rajguru et al. |
| 10,799,701 B2 | 10/2020 | Lee |
| 10,828,491 B2 | 11/2020 | Schepis et al. |
| 10,864,373 B2 | 12/2020 | Bhadra et al. |
| 10,894,159 B2 | 1/2021 | De Ridder |
| 10,926,092 B2 | 2/2021 | Esteller et al. |
| 10,953,228 B2 | 3/2021 | Perryman et al. |
| 10,967,183 B2 | 4/2021 | Yakovlev et al. |
| 11,007,364 B2 | 5/2021 | Carroll |
| 11,027,126 B2 | 6/2021 | Ackermann et al. |
| 11,071,863 B2 | 7/2021 | Torgerson |
| 11,116,965 B2 | 9/2021 | Snyder |
| 11,116,975 B2 | 9/2021 | Oron et al. |
| 11,167,129 B2 | 11/2021 | Parker |
| 11,213,682 B2 | 1/2022 | Syed Shah et al. |
| 11,235,146 B2 | 2/2022 | Boggs et al. |
| 11,247,053 B2 | 2/2022 | Rajguru et al. |
| 11,253,705 B1 | 2/2022 | John |
| 11,278,718 B2 | 3/2022 | Faltys et al. |
| 11,311,726 B2 | 4/2022 | Vansickle et al. |
| 11,331,489 B2 | 5/2022 | Johanek |
| 11,331,493 B2 | 5/2022 | Pivonka et al. |
| 11,344,726 B2 | 5/2022 | Bennett et al. |
| 11,344,729 B1 | 5/2022 | Single et al. |
| 11,413,458 B2 * | 8/2022 | Fang .................. A61N 1/36021 |
| 2002/0055779 A1 | 5/2002 | Andrews |
| 2002/0198572 A1 | 12/2002 | Weiner |
| 2003/0144709 A1 | 7/2003 | Zabara et al. |
| 2004/0015205 A1 | 1/2004 | Whitehurst et al. |
| 2004/0111139 A1 | 6/2004 | McCreery |

(56) References Cited

U.S. PATENT DOCUMENTS

| | | |
|---|---|---|
| 2004/0147977 A1 | 7/2004 | Petrofsky |
| 2004/0243182 A1 | 12/2004 | Cohen et al. |
| 2005/0131485 A1 | 6/2005 | Knudson et al. |
| 2005/0137648 A1 | 6/2005 | Cosendal et al. |
| 2005/0143789 A1 | 6/2005 | Whitehurst et al. |
| 2005/0149148 A1 | 7/2005 | King |
| 2005/0149154 A1 | 7/2005 | Cohen et al. |
| 2006/0025832 A1 | 2/2006 | O'Keeffe et al. |
| 2006/0030919 A1 | 2/2006 | Mrva et al. |
| 2006/0184211 A1 | 8/2006 | Gaunt et al. |
| 2006/0195158 A1 | 8/2006 | Cory |
| 2006/0270944 A1 | 11/2006 | King et al. |
| 2006/0271137 A1* | 11/2006 | Stanton-Hicks ..... A61N 1/0551 607/118 |
| 2007/0043400 A1 | 2/2007 | Donders |
| 2007/0142863 A1 | 6/2007 | Bradley |
| 2007/0185549 A1 | 8/2007 | Zdeblick |
| 2008/0027505 A1 | 1/2008 | Levin et al. |
| 2008/0046055 A1 | 2/2008 | Durand et al. |
| 2008/0086180 A1 | 4/2008 | Ben-Ezra et al. |
| 2008/0172116 A1 | 7/2008 | Mrva et al. |
| 2008/0183226 A1 | 7/2008 | Buras et al. |
| 2008/0228194 A1 | 9/2008 | Westlund et al. |
| 2008/0319511 A1 | 12/2008 | Pless |
| 2009/0069738 A1 | 3/2009 | Rossing et al. |
| 2009/0083070 A1 | 3/2009 | Giftakis et al. |
| 2009/0204173 A1 | 8/2009 | Fang et al. |
| 2009/0281595 A1 | 11/2009 | King et al. |
| 2010/0121408 A1 | 5/2010 | Imran et al. |
| 2010/0152808 A1 | 6/2010 | Boggs, II |
| 2010/0168820 A1 | 7/2010 | Maniak et al. |
| 2010/0211135 A1 | 8/2010 | Caparso et al. |
| 2010/0241190 A1* | 9/2010 | Kilgore ................ A61N 1/0551 607/48 |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274326 A1 | 10/2010 | Chitre et al. |
| 2011/0071593 A1 | 3/2011 | Parker et al. |
| 2011/0230701 A1 | 9/2011 | Simon et al. |
| 2012/0016439 A1 | 1/2012 | Alataris et al. |
| 2012/0083709 A1 | 4/2012 | Parker et al. |
| 2012/0083856 A1 | 4/2012 | Thacker et al. |
| 2012/0089199 A1 | 4/2012 | Bolea et al. |
| 2012/0232615 A1 | 9/2012 | Barolat et al. |
| 2012/0253261 A1 | 10/2012 | Poletto et al. |
| 2013/0035735 A1 | 2/2013 | Kroll |
| 2013/0289664 A1 | 10/2013 | Johanek |
| 2013/0289667 A1 | 10/2013 | Wacnik et al. |
| 2014/0046398 A1 | 2/2014 | Sachs et al. |
| 2014/0188186 A1 | 7/2014 | Barolat et al. |
| 2014/0228905 A1 | 8/2014 | Bolea |
| 2015/0230809 A1 | 8/2015 | Becker |
| 2016/0256685 A1 | 9/2016 | Haessler |
| 2016/0361542 A1 | 12/2016 | Kaula et al. |
| 2017/0007836 A1 | 1/2017 | Nassif |
| 2017/0095667 A1 | 4/2017 | Yakovlev et al. |
| 2017/0239486 A1 | 8/2017 | Suryavanshi |
| 2017/0319381 A1 | 11/2017 | Rogers |
| 2017/0333701 A1 | 11/2017 | Bradley et al. |
| 2017/0348532 A1 | 12/2017 | Moffitt et al. |
| 2018/0008827 A1 | 1/2018 | Dolev et al. |
| 2018/0021577 A1 | 1/2018 | Phillips |
| 2018/0043172 A1 | 2/2018 | Serrano Carmona |
| 2018/0056066 A1 | 3/2018 | Boggs et al. |
| 2018/0140835 A1 | 5/2018 | Sharma |
| 2018/0333576 A1 | 11/2018 | Rigaux |
| 2019/0151659 A1 | 5/2019 | Mishra et al. |
| 2019/0184170 A1 | 6/2019 | Knudson et al. |
| 2019/0358455 A1 | 11/2019 | Lin et al. |
| 2019/0358466 A1 | 11/2019 | Leung et al. |
| 2019/0374779 A1 | 12/2019 | Kilgore et al. |
| 2020/0324113 A1 | 10/2020 | Fisher et al. |
| 2020/0368518 A1 | 11/2020 | Vera-Portocarrero et al. |
| 2021/0069501 A1 | 3/2021 | Molnar et al. |
| 2021/0113840 A1 | 4/2021 | Bhadra et al. |
| 2021/0154478 A1 | 5/2021 | Hincapie Ordonez et al. |
| 2021/0220642 A1 | 7/2021 | Fang et al. |
| 2021/0236820 A1 | 8/2021 | Parker et al. |
| 2021/0244952 A1 | 8/2021 | Iorio et al. |
| 2021/0252288 A1 | 8/2021 | Lin et al. |
| 2021/0260381 A1 | 8/2021 | Kilgore et al. |
| 2021/0283398 A1 | 9/2021 | Kibler et al. |
| 2021/0283401 A1 | 9/2021 | Tai |
| 2021/0308456 A1 | 10/2021 | Gliner et al. |
| 2021/0370054 A1 | 12/2021 | Snyder |
| 2022/0008723 A1 | 1/2022 | Hsu et al. |
| 2022/0016421 A1 | 1/2022 | Boggs et al. |
| 2022/0023634 A1 | 1/2022 | Parker et al. |
| 2022/0023635 A1 | 1/2022 | Pepin et al. |
| 2022/0023648 A1 | 1/2022 | Doan et al. |
| 2022/0032060 A1 | 2/2022 | Bhadra et al. |
| 2022/0072310 A1 | 3/2022 | Syed Shah et al. |
| 2022/0152393 A1 | 5/2022 | Kent et al. |
| 2022/0176108 A1 | 6/2022 | Linden et al. |
| 2024/0001122 A1 | 1/2024 | Syed Shah et al. |

FOREIGN PATENT DOCUMENTS

| | | |
|---|---|---|
| EP | 3219357 A1 | 9/2017 |
| JP | 2009522015 A | 6/2009 |
| JP | 2012130579 A | 7/2012 |
| WO | WO00/61222 A1 | 10/2000 |
| WO | WO2005/105202 A1 | 11/2005 |
| WO | WO2007/117347 A1 | 10/2007 |
| WO | WO2009/079270 A1 | 6/2009 |
| WO | WO2012/159002 A8 | 11/2012 |
| WO | WO2018/033855 A1 | 2/2018 |
| WO | WO2018/067239 A1 | 4/2018 |
| WO | WO2018/106839 A2 | 6/2018 |
| WO | WO2020/041323 A1 | 2/2020 |
| WO | WO2020/243096 A1 | 12/2020 |
| WO | WO2021/003151 A1 | 1/2021 |
| WO | WO2021/111371 A1 | 6/2021 |
| WO | WO2021/216568 A1 | 10/2021 |

OTHER PUBLICATIONS

Ackermann et al.; Electrical conduction block in large nerves: high frequency current delivery in the nonhuman primate; Muscle and Nerve. 43(6); pp. 897-899; Jun. 2011.

Becker et al.; Essentials of local anesthetic pharmacology; Anesthesia progress; 53(3); pp. 98-109; Sep. 2006.

Bhadra et al.; High-frequency electrical conduction block of mammalian peripheral motor nerve; Muscle and Nerve; 32(6); pp. 782-790; Dec. 2005.

Bhadra et al.; Simulation of high-frequency sinusoidal electrical block of mammalian myelinated axons; Journal of Computational Neuroscience; 22(3); pp. 313-326; Jun. 1, 2007.

Bouaziz et al., Neurologic complication of peripheral neural blockade. In Cousins and Bridenbaugh's Neural blockade in clinical anesthesia and pain medicine, 4th ed. (Cousins et al., eds.); Ch. 20; Lippincott Williams and Wilkins; pp. 464-477; (the year of publication is sufficiently earlier than the effective U.S. filing date and any foreign priority date so that the particular month of publication is not in issue) 2009.

Cleeland et al.; Pain assessment: global use of the Brief Pain Inventory; Annals, Academy of Medicine, Singapore; 23(2); pp. 129-138; Mar. 1994.

Dickinson et al.; Maldynia: pathophysiology and management of neuropathic and maladaptive pain a report of the AMA Council on Science and Public Health; Pain Medicine; 11(11); pp. 1635-1653; Nov. 1, 2010.

Dworkin et al.; Interpreting the clinical importance of treatment outcomes in chronic pain clinical trials: IMMPACT recommendations; The Journal of Pain; 9(2); pp. 105-121; Feb. 1, 2008.

(56) References Cited

OTHER PUBLICATIONS

Fisher et al.; Chronic stability and selectivity of four-contact spiral nerve-cuff electrodes in stimulating the human femoral nerve; J. Neural Eng.; 6(4); pp. 1-16; Aug. 2009.
Flor et al.; Phantom limb pain: a case of maladaptive CNS plasticity? Nature Reviews Neuroscience; 7(11); pp. 873-881; Nov. 2006.
Fyfe, N.; An audit of amputation levels in patients referred for prosthetic rehabilitation; Prosthetics and Orthotics International; 14(2); pp. 67-70; Aug. 1990.
Gerges et al.; Frequency- and amplitude-transitioned waveforms mitigate the onset response in high-frequency nerve block; Journal of Neural Engineering; 7(6); pp. 1-17; Dec. 2010.
Guse et al.; Outcomes of the surgical treatment of peripheral neuromas of the hand and forearm: a 25-year comparative outcome study; Annals of plastic surgery; 71(6); pp. 654-658; (abstract) Dec. 1, 2013.
Hadzic et al.; Neurologic complications of peripheral nerve blocks. In Peripheral nerve blocks: principles and practice, 3rd ed. (Hadzic and Vloka, eds.); Ch. 6; New York: McGraw-Hill; pp. 67-77; Sep. 20, 2004.
Haroutounian et al.; Primary afferent input critical for maintaining spontaneous pain in peripheral neuropathy; Pain; 155(7); pp. 1272-1279 (abstract); Jul. 1, 2014.
Hsu et al.; Postamputation pain: epidemiology, mechanisms, and treatment; Journal of Pain Research; 6; pp. 121-136; Feb. 12, 2013.
Keller et al.; Validity of the brief pain inventory for use in documenting the outcomes of patients with noncancer pain; The Clinical Journal of Pain; 20(5); pp. 309-318; Sep. 1, 2004.
Kilgore et al.; Block of mammalian motor nerve conduction using high frequency alternating current; 10th Annual Conference of International FES Society; Montreal, Canada; pp. 479-481; Jul. 2005.
Kilgore et al.; Nerve conduction block utilizing high-frequency alternating current; Med. Biol. Eng. Comput.; 42(3); pp. 394-406; May 1, 2004.
Kilgore et al.; Reversible nerve conduction block using kilohertz frequency alternating current; Neuromodulation: Technology at the Neural Interface; 17(3); pp. 242-255; Apr. 2014.
Kumar et al.; Spinal cord stimulation versus conventional medical management for neuropathic pain: A multicentre randomised controlled trial in patients with failed back surgery syndrome; Pain; 132(1-2); pp. 179-188; Nov. 1, 2007.
Leland et al.; American war and military operations casualties: lists and statistics. Congressional Research Service; CRS Report to Congress; RL32492; pp. 1-30; Feb. 26, 2010.
Lewin-Kowalik et al.; Prevention and management of painful neuroma; Neurol Med Chir (Tokyo); 46(2); pp. 62-68; Feb. 2006.
Melzack et al.; Pain mechanisms: a new theory; Science; 150(3699); pp. 971-979; Nov. 19, 1965.
Miles et al.; Effects of ramped amplitude waveforms on the response of high-frequency mammalian nerve block; Journal of Neural Engineering; 4(4); pp. 390-398; Nov. 12, 2007.
Naples et al.; A spiral nerve cuff electrode for peripheral nerve stimulation; IEEE Transactions on Biomedical Engineering; 35(11); pp. 905-916; Nov. 1988.
Narang et al.; Functional capabilities of lower limb amputees; Prosthetics and Orthotics International; 8(1); pp. 43-51; Jan. 1, 1984.
NLLIC Staff. Fact Sheet. Amputation Statistics by Cause Limb Loss in the United States. Amputee Coalition of America (2008) 2 pages; retrieved from internet site http://www.amputee-coalitionsorg/fact_sheets/amp_stats_cause.pdf; Accessed Aug. 26, 2014; (the year of publication is sufficiently earlier than the effective U.S. filing date and any foreign priority date so that the particular month of publication is not in issue) 2008.
North et al.; Spinal cord stimulation versus re-operation in patients with failed back surgery syndrome: an international multicenter randomized controlled trial (EVIDENCE study); Neuromodulation: Technology at the Neural Interface; 14(4); pp. 330-336; Jul. 2011.
Page et al.; Oral Posters—Intrathecal Drug Delivery for Pain and Spasticity: 2013 1630-1640; Spine; Jun. 11, 2004. Effect of intrathecal intermittent boluses and morphine concerntration on the incidence of inflammatory mass in a canine model; International Modulation Society; pp. 272-273; Jun. 11, 2013.
Pohjolainen et al.; Prosthetic use and functional and social outcome following major lower limb amputation; Prosthetics and Orthotics Intl.; 14(2); pp. 75-79; Jan. 1, 1990.
Polasek et al.; Stimulation stability and selectivity of chronically implanted multicontact nerve cuff electrodes in the human upper extremity; IEEE Transactions on Neural Systems and Rehabilitation Engineering: 17(5); pp. 428-437; Oct. 2009.
Saper et al.; Occipital nerve stimulation for the treatment of intractable chronic migraine headache: ONSTIM feasibility study; Cephalalgia; 31(3); pp. 271-285; Feb. 2011.
Schoppen et al.; Physical, mental, and social predictors of functional outcome in unilateral lower-limb amputees; Arch Phys Med Rehabil; 84(6); pp. 803-811; Jun. 1, 2003.
Sikka; Facial expression analysis for estimating pain in clinical settings; In Proceedings of the 16th International Conference on Multimodal Interaction; pp. 349-353; Nov. 2014.
Soin et al.; High-frequency electrical nerve block for post amputation pain: a pilot study; Neuromodulation; 16(5); 9 pages; Sep. 1, 2013.
Soin et al.; Feasibility study on high-frequency electrical nerve block for amputation pain; Neuromodulation; 14(6); p. 561; Nov. 1, 2011.
Subedi et al.; Phantom limb pain: mechanisms and treatment approaches; Pain Research and Treatment; Article ID 864605; 8 pages; (the year of publication is sufficiently earlier than the effective U.S. filing date and any foreign priority date so that the particular month of publication is not in issuee) 2011.
Vaso et al.; Peripheral nervous system origin of phantom limb pain; PAIN; 155(7); pp. 1384-1391; Jul. 1, 2014.
Waataja et al.; Effects of high-frequency alternating current on axonal conduction through the vagus nerve; J. Neural Eng.; 8(5); pp. 1-7; Sep. 15, 2011.
Ziegler-Graham et al.; Estimating the Prevalence of Limb Loss in the United States: 2005 to 2050; Arch Phys Med Rehabil; 89(3); pp. 422-429; Mar. 1, 2008.

* cited by examiner

FIG 8: Summary of Feasibility Study Results
Electrical Nerve Block for Amputation Pain

| Subject | 1 | 2 | 3 | 4 | 5 |
|---|---|---|---|---|---|
| Gender, age | Male, 37 | Male, 54 | Female, 53 | Male, 76 | Male, 52 |
| Cause of amputation | Dysvascular | Dysvascular | Infection | Trauma | Trauma |
| Level of Amputation | Below knee | Above knee | Above knee | Below knee | Above knee |
| Nerve blocked | Tibial | Sciatic | Sciatic | Tibial | Sciatic |
| Spontaneous pain intensity at each visit | 3,3,3 | 0,0,0,0 | 0,0 | 2,3,7,7 | 0,7,7 |
| Induced pain intensity by pressing the neuroma | Not tried | 9 | 7 | 5 | 8 |
| In-clinic test result: number of sessions with significant/partial/no pain reductions | 1/2/5 | 3/1/2 | 0/3/1 | 6/1/0 | 7/0/0 |
| At-home use result: number of sessions with significant/partial/no pain reductions | 0/0/1 | Not used | Not used | 13/0/0 | 4/0/0 |
| Conclusion | Success in clinic | Success in clinic | Not successful | Complete success | Complete success |

FIG. 8

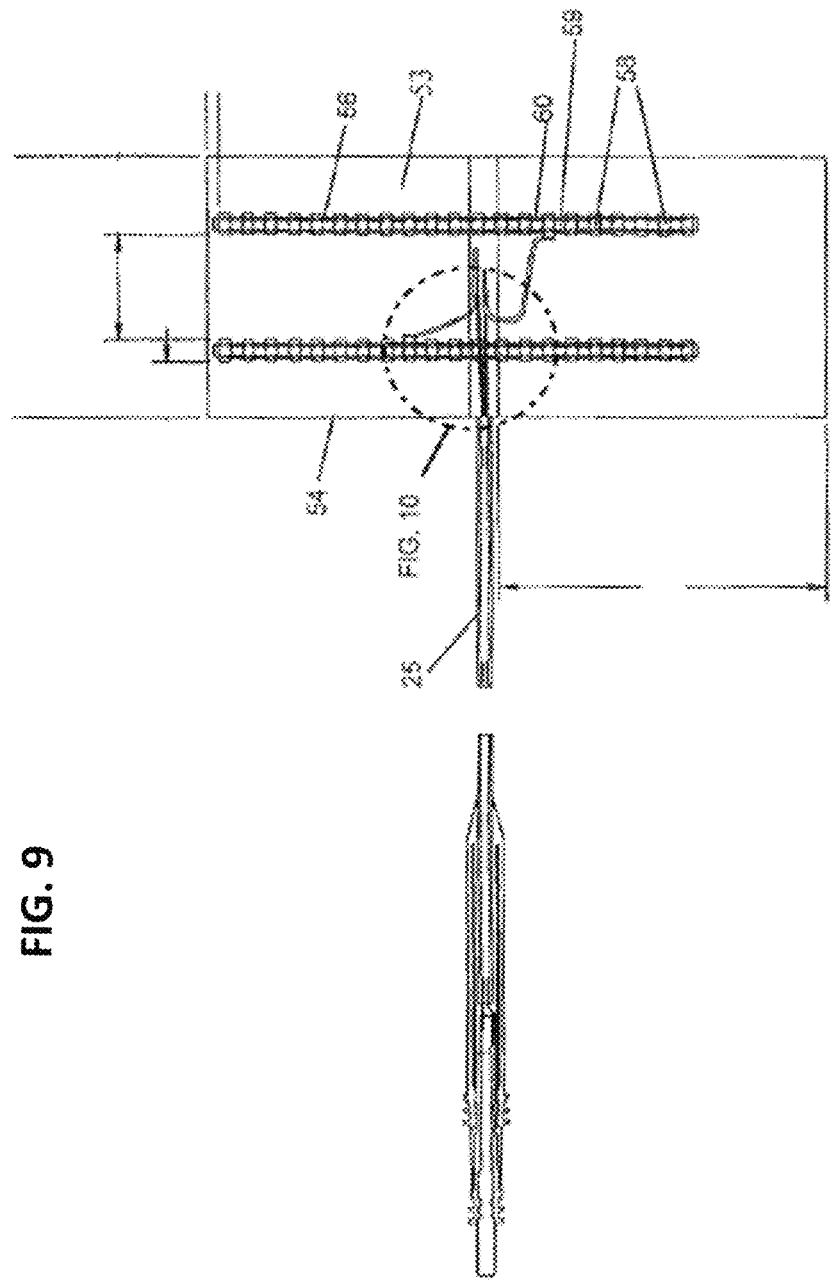

NERVE CUFF ELECTRODE FOR NEUROMODULATION IN LARGE HUMAN NERVE TRUNKS

CROSS REFERENCE TO RELATED APPLICATIONS

This application is a continuation of U.S. patent application Ser. No. 17/009,541, filed Sep. 1, 2020, now U.S. Patent Application Publication No. 2020/0391032, which claims priority as a continuation-in-part to U.S. patent application Ser. No. 15/510,824, filed on Mar. 13, 2017, now U.S. Pat. No. 10,758,723, which is a national phase application under 35 U.S.C. 371 of International Patent PCT/US2014/055374, filed Sep. 12, 2014, now International Publication No. WO 2016/039768, which is a continuation-in-part of U.S. patent application Ser. No. 14/276,200 filed May 13, 2014, now U.S. Pat. No. 8,983,612, which is a continuation of U.S. patent application Ser. No. 13/474,926 filed May 18, 2012, now U.S. Pat. No. 8,731,676, which claims priority to U.S. Provisional Patent Application No. 61/487,877 filed May 19, 2011, each of which is expressly incorporated by reference herein in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Methods and apparatuses for high frequency reversable blocking of a sensory nerve of a patient. In particular, described herein are nerve cuffs and systems including nerve cuffs that may be used for high-frequency (e.g., 5 kHz to 50 kHz) block of nerve transmission to treat pain.

BACKGROUND

It would be helpful to prevent unwanted and/or uncoordinated generation of nerve impulses which may otherwise be a disabling factor in some medical conditions. Uncoordinated motor signals may produce spasticity in stroke, cerebral palsy, multiple sclerosis, and other conditions and may lead to pain, including pain resulting from amputation. The uncoordinated signals may result in the inability to make desired functional movements. Involuntary motor signals in conditions including tics, choreas, and so on, may produce unwanted movements. Unwanted sensory signals can cause pain.

It would be beneficial to block, and in particular, reversibly block unwanted neural activity. In particular, it would be beneficial to block such activity without the use of chemical or longer-lasting means. Described herein are methods and apparatuses (e.g., systems, electrodes, etc.) for electrical modulation to treat a patient that may address these needs.

SUMMARY OF THE DISCLOSURE

Described herein are methods and apparatuses for ameliorating sensory nerve pain. In general, these method may include: connecting a waveform generator operatively to an implanted electrode contacting a trunk of a sensory peripheral nerve (e.g., a nerve trunk having a diameter exceeding 3 mm and up to 12 mm) in the patient, resulting in prevention of action potential transmission in the nerve upon application of a waveform of at least 5 kHz up to 50 kHz where the frequency blocks but does not stimulate and is not used to generate an action potential in a nerve but rather to block conduction of an action potential at one of a voltage ranging from 4 Vpp to 20 Vpp, or a current ranging from 4 mApp to 26 mApp at a plurality of contact surfaces with the nerve trunk for an interval sufficient to effect substantially immediate pain relief in the patient. The waveform(s) may be repeated as needed to ameliorate nerve pain.

In particular, these methods and apparatuses may include the use of a nerve cuff electrode to apply the stimulation to the nerve. For example, a nerve cuff electrode may include a plurality of segmented platinum contacts connected by at least one wire made of durable and biocompatible conductive material fashioned in a helical configuration. In embodiments, two such wires fashioned in a helical configuration provided redundancy. The helical configuration increased the durability of the interconnections relative to a non-helical wire or a straight wire. The inventive nerve cuff electrode provided enhanced durability, lasting on the order of 1,000,000 cycles of compression of up to 50% of diameter followed by uncompression to original diameter, compared to standard electrodes that disintegrated or broke after compression cycles on the order of 100,000 cycles. Durability is a particular problem, solved by the inventive apparatus and method, when electrodes in use are used on relatively large nerve trunks in the lower extremities, generally defined as a nerve trunk having a diameter of 3 mm or greater. This is due to repeated creasing, wrinkling, and/or breaking along their length, occurring for example when the nerve trunk is repeatedly flattened and compressed during a patient's daily activities.

The inventive nerve cuff electrode comprises a plurality of conductive nerve contact segments, with the segments having an inner surface contacting a nerve trunk and an outer surface not contacting the nerve trunk; at least a single wire of a conductive biocompatible material operatively connecting the plurality of conductive nerve contact segments thus forming a segmented strip, the wire configured as helical portions separated by non-helical portions where the non-helical portions are secured to the surface of the conductive nerve contact segments not contacting the nerve trunk; and a conductive lead capable of operatively connecting a waveform generator to at least one of the plurality of nerve contact segments. The wire helical portions are along the wire length between the conductive nerve contact segments, and the wire non-helical portions are secured to the conductive nerve contact segments by a plurality of spot welds. The wire helical portions are embedded in a non-conductive material. The helical portions are separated by non-helical portions that connects the conductive nerve contact segments. A second wire may operatively connect the plurality of nerve contact segments, with the second wire generally parallel with the first wire. In one embodiment, the conductive nerve contact segments are platinum, the wires are stainless steel, and the non-conductive material is silicone.

In one embodiment the nerve cuff electrode comprises a plurality of platinum nerve contact segments, each nerve contact segment comprising an inner surface contacting a nerve trunk and an outer surface not contacting the nerve trunk; at least two wires of a conductive biocompatible material operatively connecting the plurality of platinum nerve contact segments thus forming a segmented strip, the wires configured as helical portions separated by non-helical portions where the non-helical portions connect to the surface of the platinum nerve contact segments not contacting the nerve trunk by a plurality of spot welds, the wires embedded in a silicone sheet such that only the inner surface of the platinum nerve contact segments contacts the nerve trunk; and a conductive lead capable of operatively connecting a waveform generator to one of the plurality of platinum nerve contact segments.

One embodiment is a method of increasing durability of a nerve cuff electrode by operatively connecting a plurality of segmented conductive contacts of the electrode with at least a single wire thus forming a segmented strip, the wire configured as helical portions separated by non-helical portions where the non-helical gap portions are secured to the surface of the conductive contacts. In this embodiment, the helical portions permit repeated electrode deformations, e.g., creases, wrinkles, and/or breaks, without breaking. The segmented conductive contacts result in decreased stress on contacts.

One embodiment is a method of using a segmented nerve cuff electrode to ameliorate sensory nerve pain in a patient in need thereof. In this embodiment, a waveform generator is operatively connected to the inventive electrode in contact with a trunk of a sensory peripheral nerve having a diameter exceeding 3 mm and up to 12 mm, e.g., a sciatic nerve or a tibial nerve. In use, the method prevents action potential transmission in the nerve upon application of a waveform of at least 5 kHz up to 50 kHz at one of a voltage ranging from 4 Vpp to 20 Vpp, or a current ranging from 4 mApp to 26 mApp at a plurality of contact surfaces with the nerve trunk for an interval sufficient to effect substantially immediate pain relief in the patient. The steps can be repeated as needed to ameliorate nerve pain. The electrode contacting the nerve can be mono-, bi-, or tri-polar. The electrode cuff inner diameter may range from about 5 mm to about 12 mm. The method may also be applied to an ilioinguinal nerve to ameliorate post-surgical hernia pain, to an intercostal nerve to ameliorate pain from shingles, to a sciatic nerve to ameliorate neuropathic diabetes pain, and to an occipital nerve to ameliorate migraine pain.

One embodiment is a method of using a segmented nerve cuff electrode to effect a desired response in a patient using the above-described method. The desired response may be ameliorating spasticity of a muscle enervated by the nerve, where the patient experiences spasticity amelioration substantially immediately upon application of the electrical waveform. The desired response may be ameliorating an urge to void the bladder and the patient experiences urge amelioration substantially immediately upon application of the electrical waveform, and the nerve contacted may be a pelvic nerve.

Successful results are disclosed from a method and apparatus that uses high frequency nerve block to acutely treat peripheral pain, either acute pain or chronic pain (more than 6 months in duration), in humans by blocking nerve conduction on an action potential. Acute treatment is defined as on demand treatment with substantially immediate pain relief effect. In one embodiment, the method is used in peripheral nerves having a diameter up to about 12 mm, i.e., in relatively large nerves such as the sciatic nerve. In one embodiment, the method is used on a nerve to ameliorate a non-pain condition by therapy to a nerve, e.g., motor nerves resulting in spasticity, e.g., nerves providing an urge to void in overactive bladder.

Previous therapy for pain of peripheral origin, e.g., damaged nerves in a limb, consisted of one or a combination of the following methods.

One previous therapy was local injection of a pharmacologic anesthetic such as lidocaine. The therapeutic effect often lasts only a short time, e.g., a few hours. Repeated dosing is typically not feasible because of toxicity of the anesthetic and other reasons.

Another previous therapy was conventional electrical stimulation by surface electrodes or surgically implanted electrodes (e.g., TENS, Peripheral Nerve and Spinal Cord Stimulator). Electrical stimulation therapy is used to treat back pain and joint pain, but produces inconsistent effects. The inconsistencies are due to the indirect nature of the therapy; instead of blocking pain signals from the origin of the pain, this type of electrical stimulation activates non-pain sensory nerves to generate other types of sensation (e.g., tingling) that mask the pain sensation. Such masking is by a complex, and often unreliable, interaction of various parts of the nervous system.

A potential therapy involves reversibly blocking peripheral nerves by applying high frequency alternating current directly on a nerve trunk. Specifically, a current ranging from 5 kHz to 50 kHz was applied; this was denoted as high frequency, compared to a current of less than 1 kHz applied in the conventional electrical stimulation described above. Efficacy of the high frequency alternating current therapy in acute non-human animal experiments (frog, cat) has been reported. U.S. Pat. Nos. 7,389,145 and 8,060,208 describe in general this electrical stimulation technology. No data are described.

One embodiment of the invention discloses a method for reversibly blocking an action potential in a peripheral nerve having a diameter exceeding 3 mm and up to about 12 mm, e.g., a sciatic nerve, a tibial nerve, etc., in a patient in need thereof. The method comprises providing an electrical waveform for an interval of time sufficient to effect substantially immediate pain relief, defined generally as within about 10 min. One embodiment uses a waveform ranging from 5 kHz to 50 kHz. One embodiment uses a 10 kHz sinusoidal waveform at a current ranging from 4 mApp to 26 mApp. The electrode can be retained in a cuff encircling the desired peripheral nerve in which the action potential is to be blocked; the cuff inner diameter may range from about 5 mm to about 12 mm. The time interval may be about 10 minutes, but an interval may be selected by a magnitude sufficient to effect pain relief in the patient. In one embodiment, the electrical waveform to effect pain relief ranges from a voltage from 4 Vpp to 20 Vpp, or a current ranging from 4 mApp to 26 mApp. The time of increasing magnitude can range from about 10 seconds to about 60 seconds with a steady ramp up of voltage or current. The waveform is provided by a waveform generator that is operatively connected to the electrode implanted in the patient; such methods are known in the art.

One embodiment is a device that reversibly blocks an action potential in a relatively large nerve, i.e., a nerve with a diameter exceeding about 3 mm and up to 12 mm. The apparatus has a self-curling sheet of non-conductive material that includes a first layer, which is pre-tensioned, and a second layer, which is not pre-tensioned. The two layers are configured to form a cuff containing or holding strips of conductive material therebetween. In embodiments, the device has one, two, three, four or more segmented strips of a conductive material that are disposed adjacent, but not transverse, to one longitudinally extending edge of the self-curling sheet, each of these strips of conductive material is connected to an electrically conductive lead. In one embodiment, the device contains one strip of a conductive material, termed a monopolar configuration. In one embodiment, the device contains at least two segmented strips, connected by an electrically conductive lead, of a conductive material, termed a bipolar configuration. In one embodiment, the device contains at least three segmented strips, connected by an electrically conductive lead, of a conductive material, termed a tripolar configuration. In one embodiment, the device contains at least four segmented strips, connected by an electrically conductive lead, of a conductive material. Multiple apertures, typically circular but not necessarily so limited in shape, are disposed at periodic intervals of the inner nerve-contacting surface along the curling length of one of the two non-conductive sheets or layers of the self-curling sheet/cuff. This provides contact to the nerve by exposing and providing continuous multiple conductive contact points. The exposure may be at any interval that exposes as much of the conductive material as possible or desirable, and exceeds the contact surface area of conventional electrodes. Each of the first or top non-conductive sheet or layer and the second or bottom non-conductive sheet or layer still retains and contains the conductive material therebetween, i.e., sandwiched inside the sheets or layers, so that the conductive material is in fact retained and does not pop out or come out while providing efficient current delivery. In one embodiment the non-conductive material is silicone, the electrically conductive lead is stainless steel, and the conductive material is platinum. Other materials for each of the non-conductive material, the electrically conductive lead or wire, and the conductive material are known in the art. In use, the device is operatively connected, e.g., by an external lead or wire, to a waveform generator that provides the regulated waveform.

One embodiment is a method for treating peripheral nerve pain in a patient in need of this treatment. The above-described device encircled a particular segment of a targeted peripheral nerve, e.g., a sciatic nerve, a tibial nerve. Using a patient-implanted electrode connected to an electrical waveform generator, an electrical waveform is applied for a time interval, e.g., 10 min, sufficient to effect substantially immediate patient pain relief, e.g., within 10 min, and an extended period of pain relief up to several hours. The current in one embodiment ranges from 4 mApp to 26 mApp, and in one embodiment ranges from 4 mApp to 26 mApp.

Implementation of electrical nerve block or activation in patients for pain management or other conditions often requires a direct interfacing device with peripheral nerves in the form of a cuff wrapping around a nerve trunk.

U.S. Pat. No. 8,731,676 discloses a bipolar nerve cuff electrode with two continuous platinum strips embedded in a silicone substrate used to wrap around a nerve trunk. However, breakage of the platinum strips was found where a larger nerve trunk and/or certain anatomical characteristics (such as short stumps in above-knee amputees) were encountered. Inspections of explanted electrodes revealed that the platinum strips situated around the nerve trunk were wrinkled/creased or broken along their length due to repeated bending when the nerve trunk was compressed and flattened during daily activities.

Realizing platinum is of low mechanical strength despite its superior biocompatibility and electrical characteristics for charge delivery, a design was conceptualized with multiple segmented platinum contacts and each segment connected with wires made of a durable and biocompatible conductive material, e.g., stainless steel (SS). The total surface area of all of the platinum contacts was equivalent to that of a continuous strip by increasing the width to compensate for the gaps between the contacts.

The configuration of the wire interconnection establishes the durability and flexibility of the cuff electrode. Specifically and in one embodiment, a 7-strand of 316LVM wire was wound into a helix. A gap was created along the helix wherever it overlaps with a platinum contact. Conventional spot welding was used for connecting the wire to the platinum contact. In embodiments, two wire helices lying in parallel were employed to provide redundancy. The helices were entirely embedded in the silicone sheeting and only the outer side of the platinum contacts was exposed to the surface of the nerve trunk.

Relative to prior electrodes, the inventive segmented nerve cuff electrode had extended durability under repeated compression. Enhanced durability was demonstrated by subjecting electrodes to repetitive cycles of compressions of up to 50% of original diameter followed by decompression to original diameter, and testing for continuity across segments. Cuffs incorporating continuous platinum strips underwent compression cycles on the order of 1,000,000 cycles and remained intact.

In the inventive method, data from a human study using high frequency electrical nerve block technology for pain management are provided. In one embodiment, the result was that amputation pain was reduced. Application of 10 kHz alternating current generated by a custom generator via a custom implanted nerve electrode significantly reduced pain in the majority of patients treated by the method. The required voltage/current level is reported. The duration for achieving reliable pain relief in specific human nerves is reported. The required sequence and time to apply the electrical energy to minimize side effects is reported. The anticipated accompanying sensations and their time course is reported. The duration of pain relief after termination of the electrical current is reported. The cumulative effect of successive applications of the current on the extent of pain reduction is reported.

The apparatus was an implantable electrode operatively connected to an external or implanted waveform generator. The electrode was a spiral cuff electrode similar to that described in U.S. Pat. No. 4,602,624, more fully described below. In use, the electrode was implanted in a human mammal on a desired peripheral nerve trunk proximal to the pain source (e.g., a neuroma), such that the cuff encircled the desired peripheral nerve in which the action potential was to be blocked. The cuff inner diameter ranged from about 5 mm to about 12 mm. The sciatic nerve is known to have a relatively large nerve trunk; the diameter of the proximal part of the sciatic nerve in a human adult is about 12 mm. In one embodiment, the apparatus and method was used on the sciatic nerve to treat limb pain in above knee amputees. In one embodiment, the apparatus and method was used on the tibial nerve to treat limb pain in below knee amputees.

Any of the nerve cuffs described herein may be configured to provide strain relief. For example, the nerve cuffs may be configured to include one or more ties for securing the nerve cuff on or over the nerve. These ties may be loosely applied, and may allow self sizing of the nerve cuff on the nerve.

For example, in some variations the nerve cuff may include one or more ties for securing the cuff circumferentially around the nerve. The tie may be partially or completely circumferential. In some variations the tie is a suture. The method or apparatus may be configured so that the tie (e.g., suture loop) is loosely tied, having slack (e.g., +/−5% of the relaxed dimension of the tie (+/−10%, 15%, etc.), and not tight. Thus, the cuff may be self-sizing. The cuff, once implanted, may be encapsulated. After encapsulation (e.g. after about 2-3 weeks) the suture may be dissolved or degraded and may be less important. Adding the loose tie (e.g., suture) may prevent the cuff from opening during this initial time period, prior to encapsulation.

Any of the nerve cuffs described herein may include one or more tie regions, including, e.g., holes, channels, and/or ridges, for the tie. In some variations the tie regions may be configured to prevent the tie from coming off of the nerve cuff, while allowing the tie to biorabsorb/biodegrade within the body. For example, in some variations the tie is configured to circumferentially tie around the nerve cuff (and therefore around the nerve) to keep the nerve cuff in position. Alternatively or additionally, the nerve cuff may include tie regions (e.g., channels, ridges, etc.). In some examples the nerve cuff may be loosely tied, to allow the nerve cuff to expand slightly after implantation. The tie regions may be formed of silicone and may be integrally formed with the rest of the nerve cuff and/or may be added to the nerve cuff.

In general, the nerve cuff may be configured to allow expansion (up to about 5%, 10%, 15%, 20%, etc.) after implantation, which may accommodate swelling. For example, after implantation the nerve region in which the nerve cuff is applied may be irritated and may swell. The diameter may increase up to about 10%, (e.g. could swell a few mm diameter). The configuration of the nerve cuff may both allow the nerve cuff to expand in diameter (e.g., to slide and open up), without increasing the pressure on the nerve, while still remaining secured to the nerve, to prevent migration. The nerve cuffs described herein, even while the swelling is occurring, and the nerve cuff is expanded, may maintain intimate contact with the nerve in a predictable way. The nerve cuffs described herein may include one or more ridges or other regions that may permit the nerve cuff to expand and/or contract slightly, without losing contact, and may allow a tie (e.g., suture) to limit the expansion (e.g., to 5% or less, 10% or less, 15% or less, etc.), and prevent migration of the cuff. The nerve cuffs described herein may be sized; for example, the nerve cuff may include different diameter sizes.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 8 tabulates treatment outcomes from five patients.

FIG. 9 shows a schematic of a lead and a nerve cuff electrode in an uncurled configuration incorporating a segmented contact strip and lead.

DETAILED DESCRIPTION

Figure 1:
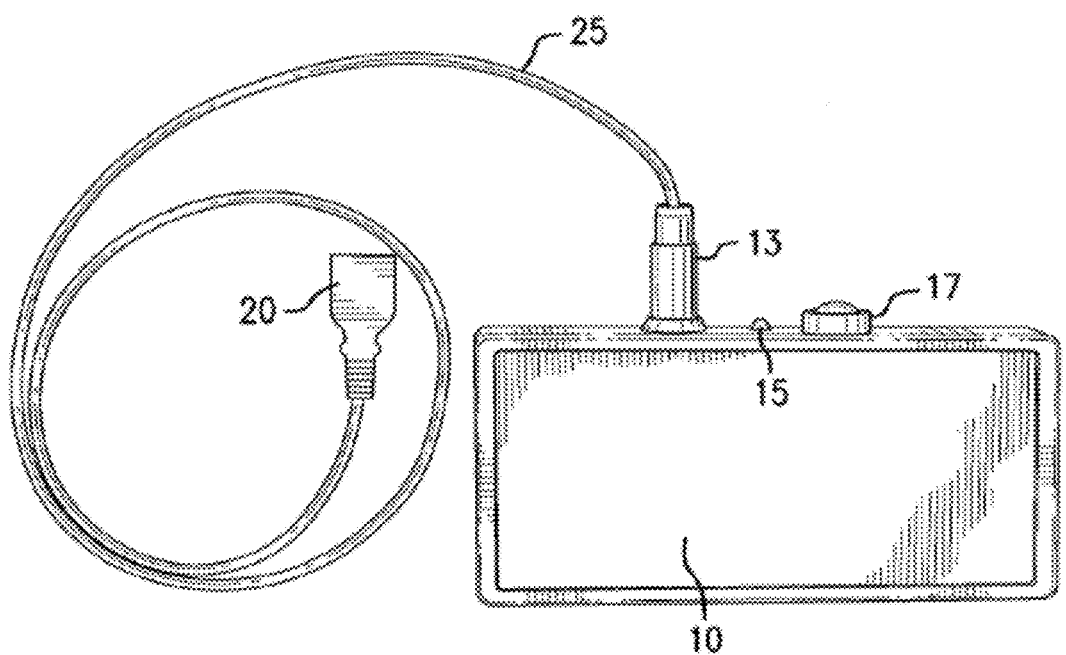
FIG. 1 is a perspective view of an external waveform generator and interconnection cable.
Figure 2:
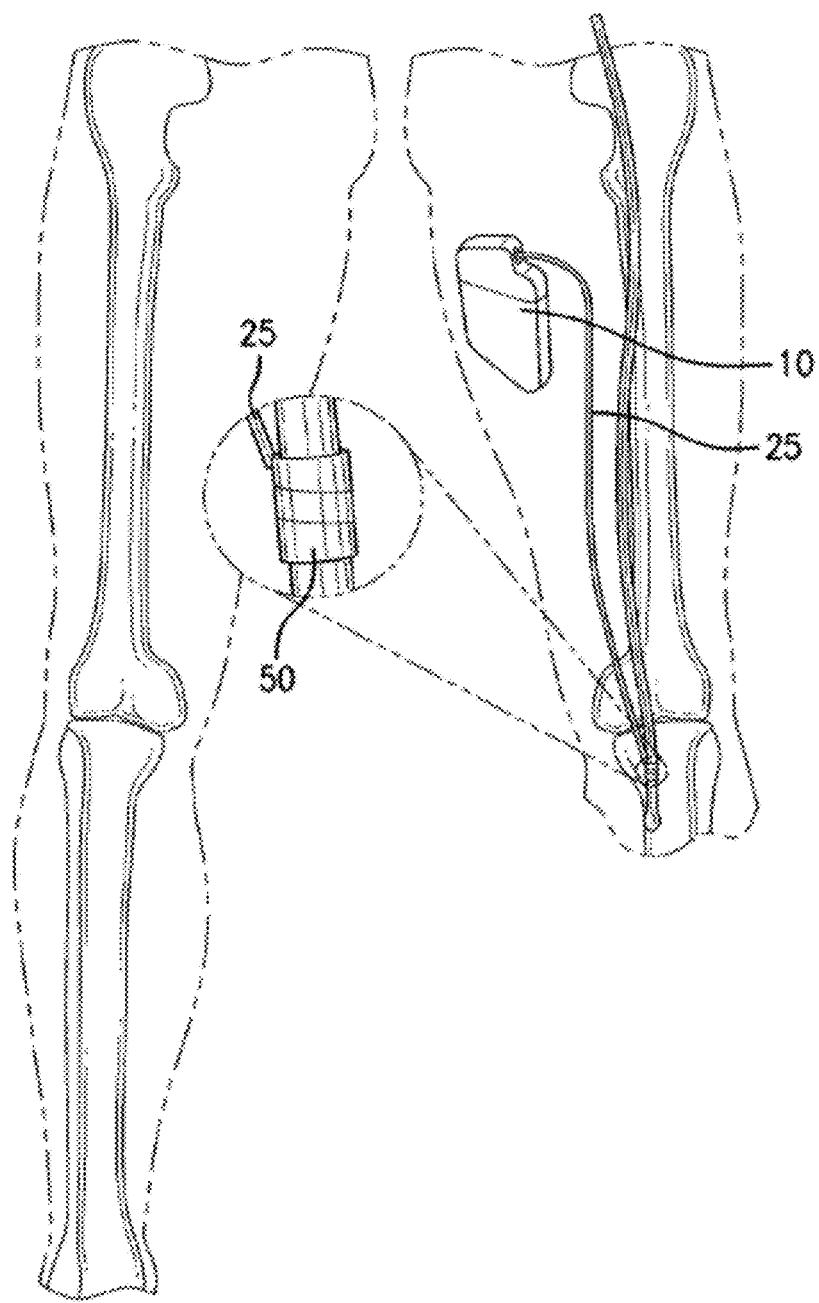
FIG. 2 shows an in-use implanted waveform generator operably connected to a nerve cuff electrode encircling a patient's nerve.

In use, the external and implanted waveform generator, shown in FIGS. 1 and 2 respectively, delivered high frequency alternating current in any form (sinusoidal wave, rectangular, other shape) sufficient to block the nerve action potential. In use, the operator selectively regulated the amount of current applied to the electrode, the duration, and any other desired parameters (e.g., continuous versus intermittent), etc. for therapy. In one embodiment, a sinusoidal waveform frequency of 10 kHz effectively and repeatedly reduced pain. In one embodiment, a sinusoidal waveform frequency ranging from 20 kHz to 30 kHz effectively reduced pain, but required about two times higher voltage and higher current for a 20 kHz sinusoidal waveform, and about three times higher voltage and higher current for a 30 kHz sinusoidal waveform, compared to that required for a 10 kHz sinusoidal waveform.

Using a sinusoidal waveform frequency of 10 kHz, patients reported a sensation threshold at a voltage ranging from 1 Vpp to 10 Vpp, and at a current ranging from 1 mApp to 16 mApp. The sensation threshold was the minimum stimulation at which a patient indicated that s/he feels a sensation due to the applied current, e.g., a patient may feel a tingling sensation.

Indication of a sensation threshold does not indicate pain relief, which is defined broadly as any pain mitigation or amelioration including but not limited to complete pain relief. Using a sinusoidal waveform of 10 kHz, the patient's relief from pain was achieved at a voltage ranging from 4 Vpp to 20 Vpp, and at a current ranging from 4 mApp to 26 mApp. The interval between the two parameters (the voltage/current required to be applied to achieve a sensation threshold, versus the voltage/current required to be applied to achieve pain relief) was optimally achieved by a conservative steady ramping up over a range from about 10 seconds to about 60 seconds. This minimized or prevented the patient from experiencing pain or other undesirable sensations at the outset of therapy.

Figure 3B:
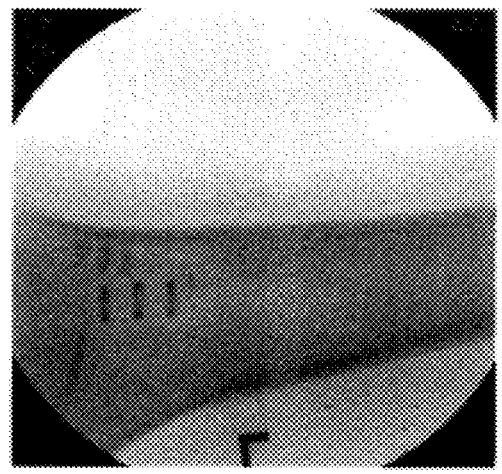
FIGS. 3A and 3B are a photograph on the implanted cuff and electrode, and a confirmatory fluoroscopy image of same, respectively.
Figure 3A:
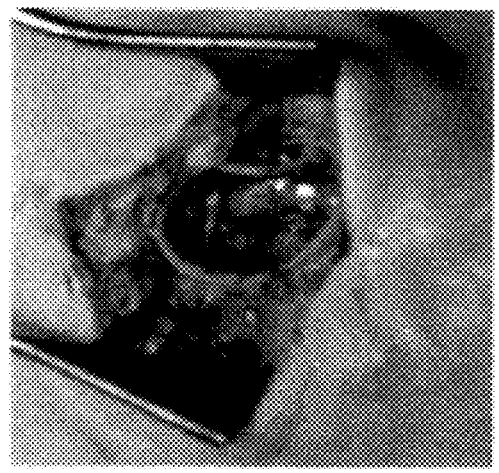

In one embodiment, the electrode was implanted on the tibial nerve, as shown in FIG. 3A. Proper implantation was verified by fluoroscopy visualization, as shown in FIG. 3B.

In one of five patients experiencing pain post lower-limb amputation, the extent of baseline pain intensity and relief of this pain by a self-administered narcotic pill were compared to the extent of each of baseline pain intensity and relief of this pain using the disclosed nerve block apparatus and method was self-assessed over a 21 consecutive day period. The patient self-assessed pain intensity using a 0-10 scale where 0 is no pain and 10 is as bad as it could be. The narcotic was hydrocodone/APAP formulated as a tablet at a dose of 10 mg/325 mg. The patient self-administered the tablet orally as needed.

When self-administering the electrical nerve block therapy, the parameters over which the patient did not have control were the amount of current applied, and the duration of each administration period. The parameters over which the patient did have control were the time(s) during the 24 hour period to self-administer the therapy, and the time interval between the administrations. In one embodiment, each treatment was for 10 minutes. In one embodiment, one self-administered electrical treatment for 10 minutes was immediately followed by at least one additional self-administered electrical treatment for 10 minutes to result in cumulative pain reduction effect. The amount of current/voltage applied during each interval ranged from 4 mApp to 26 mApp/4 Vpp to 20 Vpp, respectively.

Figure 5:
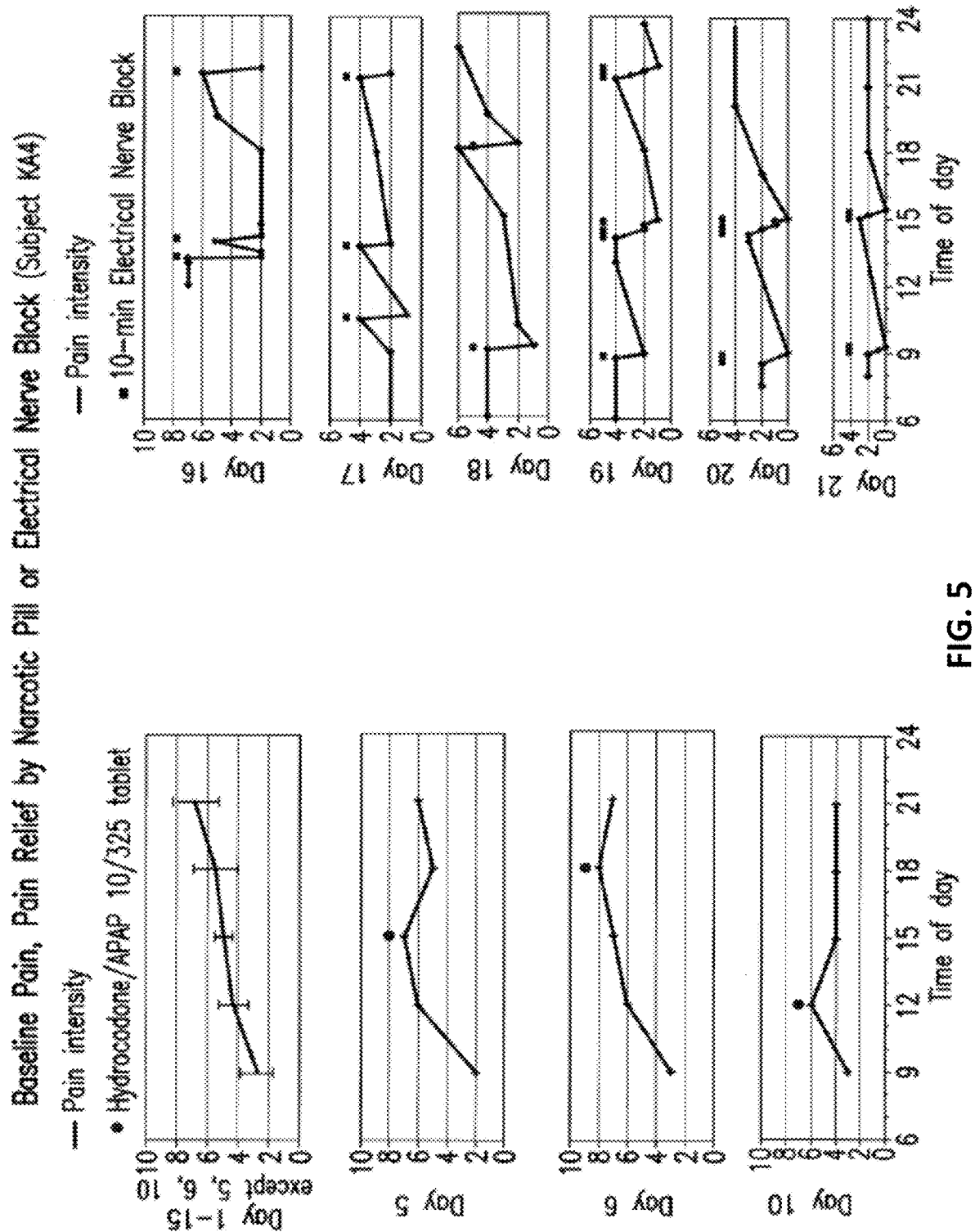
FIG. 5 graphs one patient's pain relief comparing use of the invention versus drug treatment.
Figure 6:
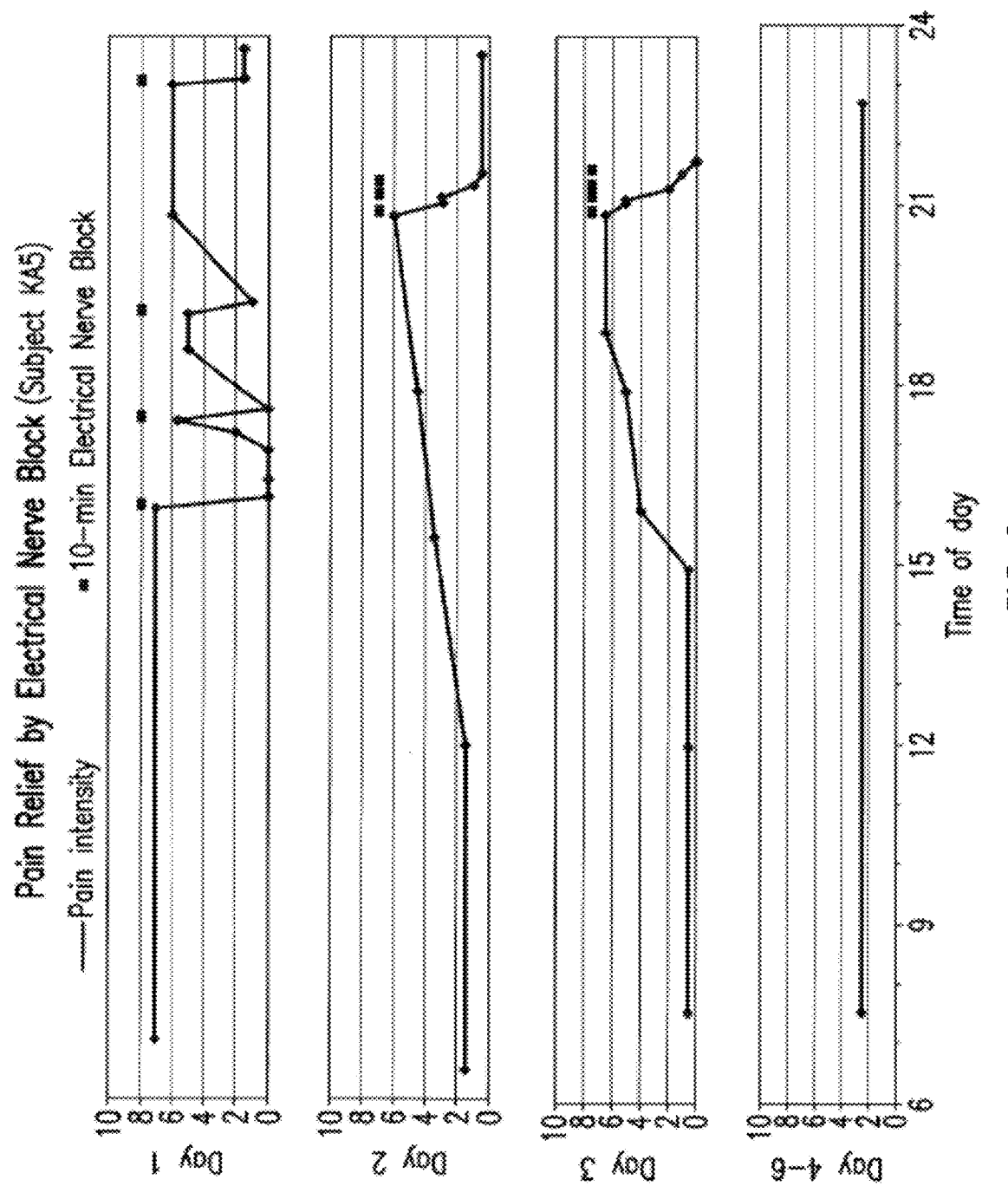
FIG. 6 graphs one patient's pain intensity and pain relief using the invention.

Specific selected data for each of two patients are shown in FIGS. 5 and 6 respectively. A summary of the results for all of the five patients is shown in FIG. 8.

The patients reported that they experienced pain mitigation within minutes of treatment onset. The patients reported that sensations such numbness, tingling, and pulling, subsided within minutes after treatment onset. The patients reported that, after a 10 min treatment (application of electrical blocking current), they experienced pain reduction that was sustained up to several hours after cessation of treatment.

A description of various embodiments of the electrode used for nerve conduction block is as follows. They differ from the use of the apparatus disclosed in Naples U.S. Pat. No. 4,602,624. Naples' electrode is used to stimulate, i.e., excite, activate, generate, an action potential in a nerve having a diameter of about 1 mm to about 3 mm. In Naples, four sets of rectangular-shaped electrodes constitute the contact points that are sandwiched between two layers of a non-conductive material such as silicone. The layers of non-conductive material were self-curling. The conductive contact points were disposed at uniform intervals therebetween at sites on the inner circumference of a first resiliently extensible layer. The conductive contact points are connected by conductive wires or leads, e.g., stainless steel wires. The layers have openings (windows) in the non-conductive material to expose the conductive contact points to the nerve upon selective regulation, in this case, activation to initiate an action potential. The distance between the openings (separation distance) and curling length of the layers is proportional to the nerve diameter.

In attempting to block an action potential in nerves having a diameter exceeding about 3 mm, the previously described apparatus and method is inadequate. This is because a simple scale-up of the aforementioned design did not permit adequate current flow that is necessary to block conduction of an action potential in a nerve that has a relatively larger diameter as compared to a typical nerve which has a diameter that does not exceed about 3 mm. For example, the sciatic nerve in an adult human has a diameter exceeding about 3 mm; it can be up to 12 mm diameter. The sciatic nerve is a frequent source of pathology and often requires therapy. The inventive method was used on nerves having a diameter exceeding about 3 mm for nerve conduction block.

In one embodiment the inventive method was used on nerves having a diameter between about 1 mm and about 8 mm. In one embodiment the inventive method was used on nerves having a diameter between about 3 mm and about 10 mm. In one embodiment the inventive method was used on nerves having a diameter between about 8 mm and about 12 mm. In one embodiment the inventive method was used on nerves having a diameter up to about 12 mm. The inventive method blocked an action potential in a nerve, including the sciatic nerve, and thus ameliorated and/or mitigated peripheral nerve pain. The inventive method was not used to generate an action potential in a nerve; rather, it was used to block conduction of an action potential. Blocking conduction of an action potential in a nerve, versus stimulating an action potential in a nerve, requires higher current, and hence lower resistance, at the interface between the nerve and the electrode. The inventive method used a generator that advantageously provided adequate voltage with lower power consumption. The inventive method thus minimized thermal damage to tissue from heat that was generated during its use, while providing improved efficiency.

In all embodiments, the electrode had a relatively larger contact surface with the nerve than conventional electrodes, such as Naples' electrode. As only one illustrative example used in the inventive method, the apertures were spaced at an interval ranging from 0.5 mm up to 1.9 mm. In one embodiment, the apertures were spaced at 1.0 mm intervals, defined as a center-to-center dimension between neighboring apertures.

Figure 4:
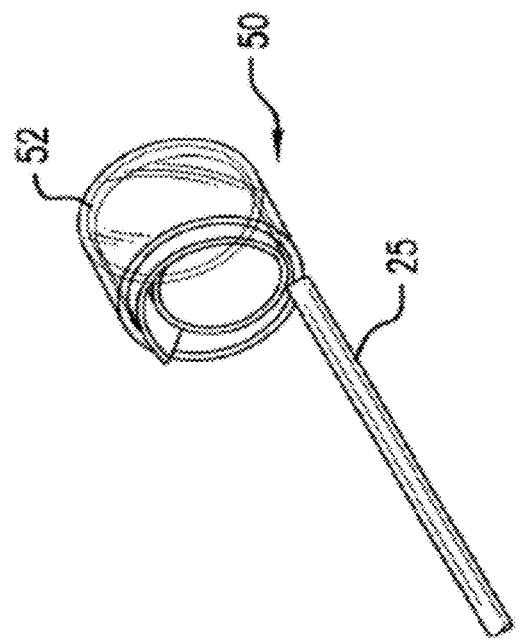
FIG. 4 schematically shows the nerve cuff electrode and lead.
Figure 7A:
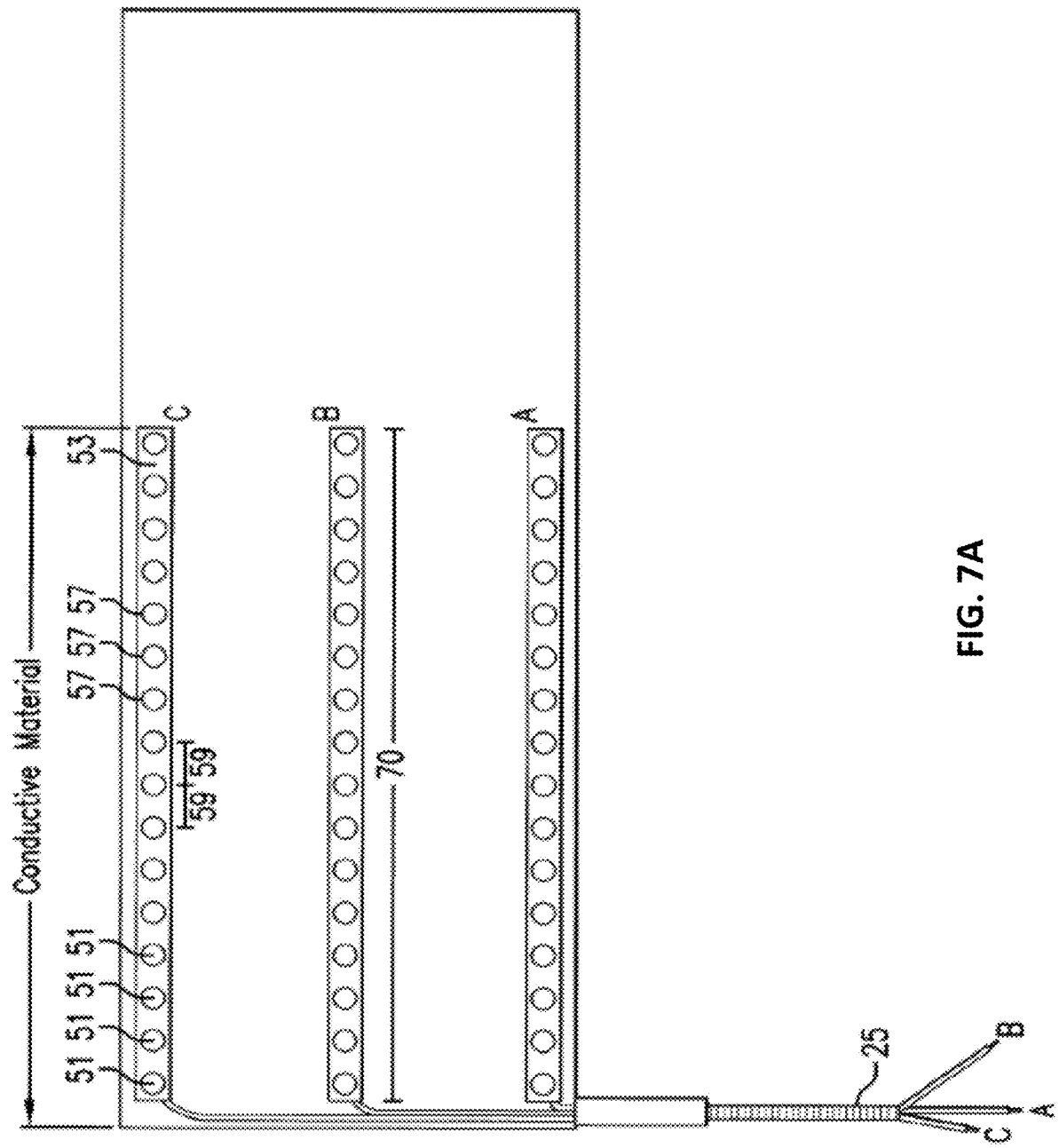
FIG. 7A shows a general schematic of a tripolar electrode in an uncurled configuration.
Figure 7B:
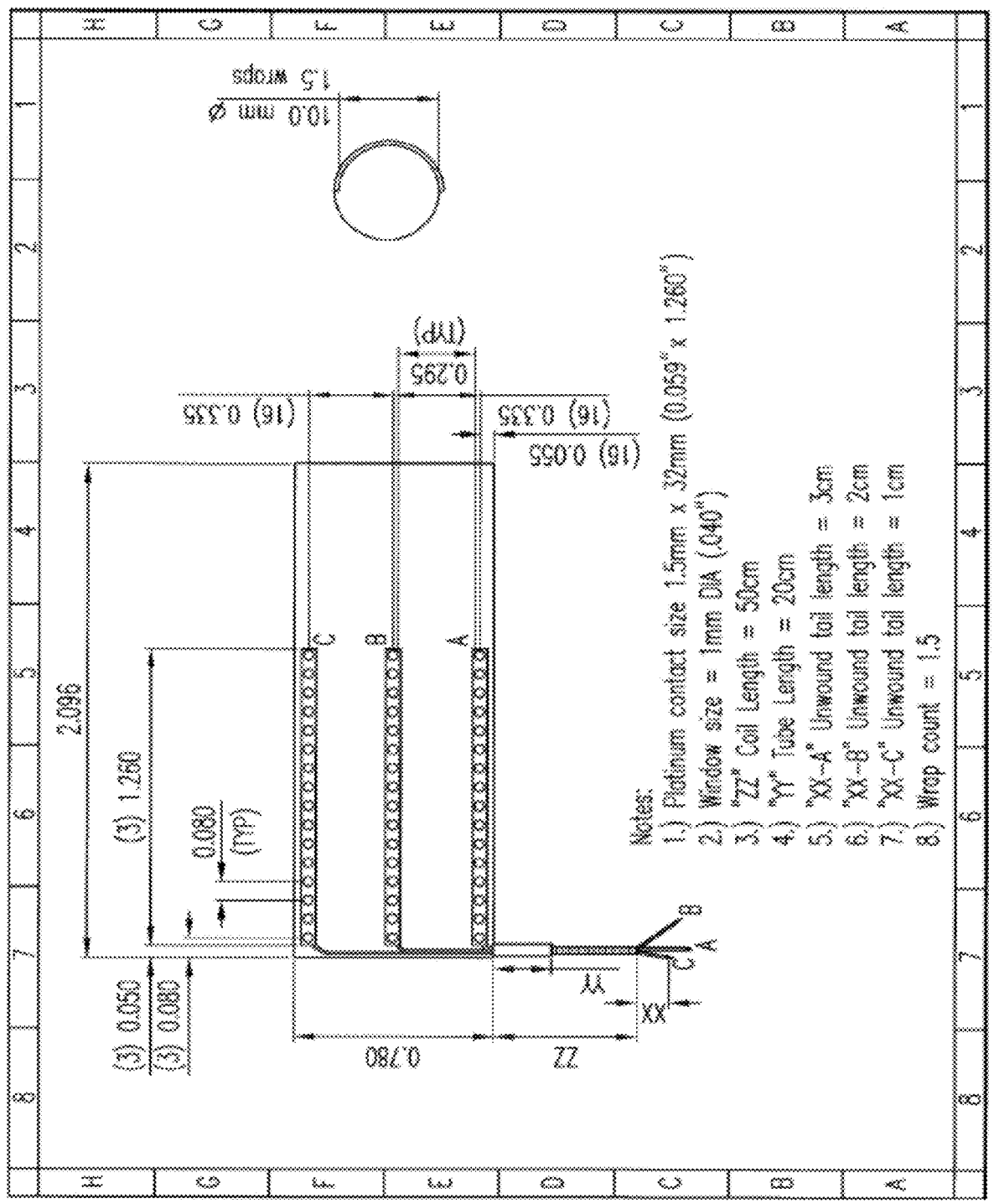
FIG. 7B shows one embodiment of FIG. 7A with specific dimensions.

As shown in FIG. 1, an external waveform generator 10 had an electrode connector 20 operatively connected with cable 25, having connector 13, LED indicator 15, and on/off indicator 17. As shown in use in FIGS. 2, 3, and 4, nerve cuff electrode 50 had conductive material 51 contained in self-curling sheet 53 and lead 25 to connect to the waveform generator 10. As best shown in FIGS. 7A, 7B, the conductive material 51 was both contained and retained within an implantable expandable spiral cuff 52, shown in FIG. 4. The cuff 52 provided the flexibility required for use to contact and regulate nerves having a diameter exceeding about 3 mm and up to about 12 mm, and provided a non-rigid contact surface with the nerve in order to minimize tissue damage.

In one embodiment, shown in general FIG. 7A and in one specific embodiment shown in FIG. 7B, the electrode contained continuous strips of conductive material 51, specifically platinum in FIG. 7B, in a sandwich configuration, with two opposing surfaces or sheets of a non-conductive material 53, specifically silicone in FIG. 7B, along the entire length of the non-conductive material 51. The non-conductive material 53 was self-curling. To provide points of contact of conductive material 51 with the nerve, around which the cuff 52 was implanted, openings or apertures 57 were created in one surface of the non-conductive material 53 at periodic intervals 59. The spacing of the intervals 59 is such that the conductive material 51 was contained and retained within the non-conductive material 53 during use, i.e., the non-conductive material does not pop out or come out, and provides sufficient exposure of the conductive material 51 for electrical contact with the nerve. In one embodiment, the openings 57 were created at 1 mm intervals. In one embodiment, the openings 57 were created at intervals ranging between about 1 mm to about less than 2 mm. The openings 57 were created in the non-conductive material 53; it was at these openings 57 that the nerve was exposed to the conductive material 51 in order to block conduction of an action potential. In a bi- or tri-polar embodiments, the distance or spacing between strips is 1:1 depending upon the nerve size to be treated; larger sized nerves can accommodate larger space between the strips. In FIG. 7A, for each electrode, the strip length with conductive material contacts 70 is shown for each of leads or wires A, B, and C. This electrode design achieved efficient current delivery to effect this blockage of the action potential. This electrode design contained and retained the conductive material 51 within the two layers of non-conductive material 53.

Figure 10:
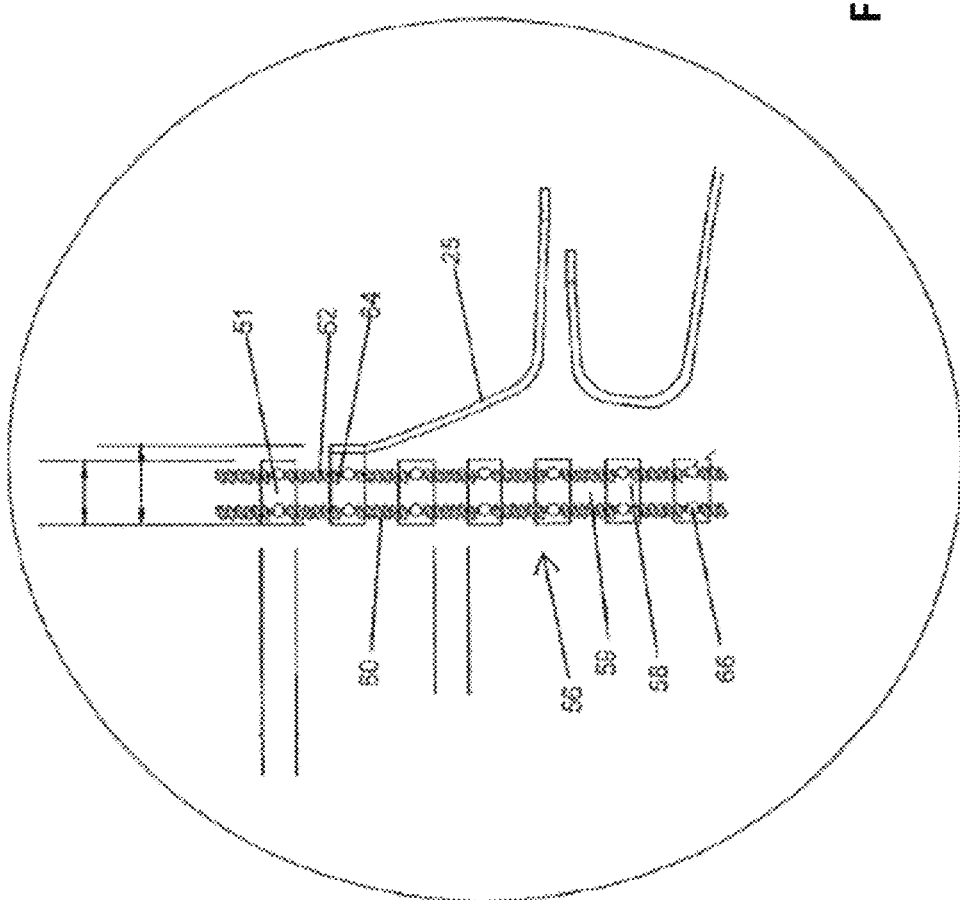
FIG. 10 shows a detailed schematic view of a segmented contact strip.

In one embodiment, shown in general in FIGS. 9 and 10, the lead 25 was operatively connected to a self-curling nerve cuff 54 with a segmented strip 56 of conductive material 51, such as platinum. Each segmented strip 56 was formed of a plurality of contact segments 58 operatively connected by wire 60, made of a durable and conductive biocompatible material such as stainless steel (SS), to form a generally linear string of the contact segments 58. The total surface area of all of the contact segments 58 may be equivalent to that of a continuous contact strip by increasing the width of the segments 58 to compensate for the spaces 59 therebetween.

Such wire 60 was wound into a helix 62, with gaps 64 therein to accommodate attachment to the contact segments 58 by conventional spot welds 66. In one embodiment, the stainless steel wire is 7-strand 316LVM wire. The helical structure of the wire 60 improves durability and flexibility of the cuff electrode by enhancing the ability of segmented strip 56 to curl about the nerve trunk in cooperation with the nerve cuff 54 by allowing the segmented strip 56 to wrap about the nerve trunk by the wire 60 without significantly bending, wrinkling, or creasing the contact segments 58 themselves. The helical structure of the wire 60 is well-suited to absorb stresses introduced by conformational changes of the nerve trunk as the patient conducts daily activities, because the helixes 62 of the wire 60 can bend and axially expand or compress in response to such environmental changes without impacting the contact segments 58 themselves.

In one embodiment, two parallel wires 60 were used to connect the contact segments 58 to provide redundancy in case one wire failed. The helixes 62 are entirely embedded in non-conductive material 53, such as silicone sheeting, such that only the side of the contact segments 58 opposite the helixes 62 is exposed to the surface of the nerve trunk.

In the embodiments shown in FIGS. 9 and 10, the nerve cuff 54 includes two segmented strips 56 of conductive material 51 disposed adjacent, but not transverse, to one longitudinally extending edge of the self-curling sheet, where each of these strips 56 is connected to the electrically conductive lead 25 (a bipolar configuration). However, the nerve cuff 54 may alternately contain only one segmented strip 56 (monopolar), or three (tripolar), four, or more segmented strips 56 as suitable for the particular application.

Although the disclosed segmented strips are described in the context of reversibly blocking an action potential in large human nerve trunks, the utility of the disclosed segmented strips 56 is broadly applicable to other nerve stimulation and/or blocking contexts, as well as to a variety of other applications where it is desirable to wrap an electric contact surface about an outer surface of a target substrate, e.g., for contact with a large nerve trunk for restoring motor or sensory function. The dimensions of the segmented strips 56, wire(s) 60, and other components are scalable.

Figure 11A:
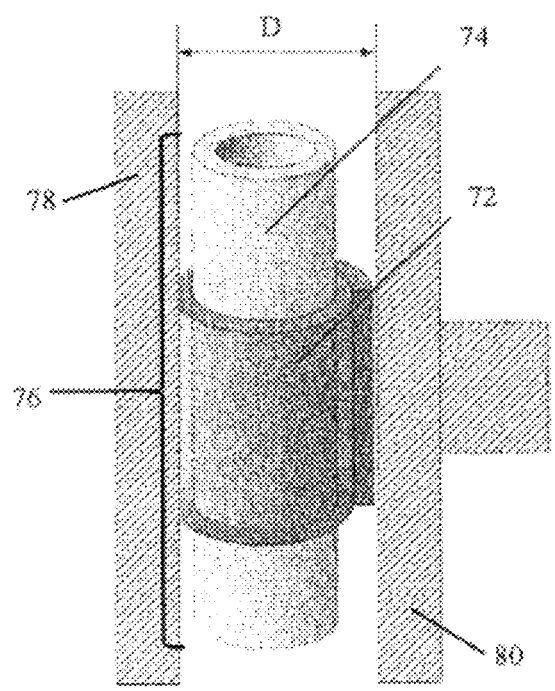
FIGS. 11A and 11B show schematic views of an apparatus to assess durability of a nerve cuff electrode.
Figure 11B:
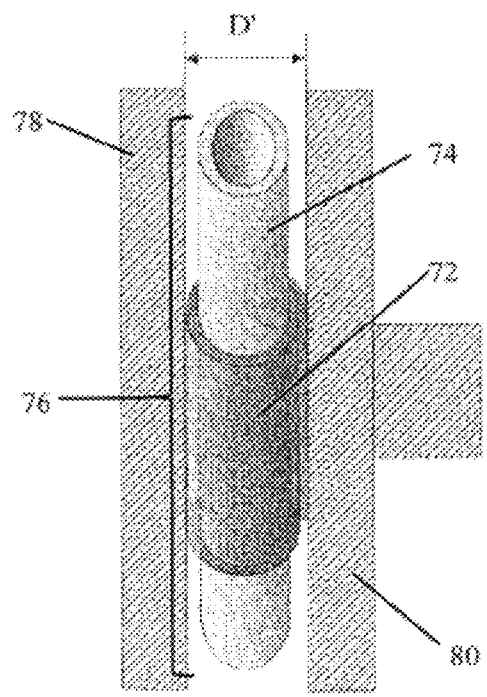

Durability for one embodiment of the inventive electrode with segmented strips 56 was assessed compared to durability of an electrode with continuous strips. The electrode with segmented strips 56 included a conductive band of segmented platinum contacts connected by a stainless steel helix. The electrode with continuous strips included a conductive band of a continuous platinum strip. In each case, the respective cuff 72 was wrapped around a length of flexible rubber tubing 74 of 3 mm to 12 mm diameter, serving as a surrogate nerve trunk to form a cuff-tube assembly 76 (FIGS. 11A-B). The cuff-tube assembly 76 was mounted between two parallel plates 78, 80 configured to move relative to each other to compress and decompress the assembly 76.

For each assessment, the cuff-tube assembly 76 was repeatedly compressed and decompressed between the plates 78, 80 between an uncompressed state (FIG. 11A), where assembly 76 has diameter D, and a compressed state (FIG. 11B), where assembly 76 has compressed diameter D'). The cuff-tube assembly 76 was compressed by 30%-50%, i.e., at 30% compression, D'=0.7×D, and at 50% compression, D'=0.5×D. Compressions were performed at 200 cycles per minute. During these assessments, the cuff-tube assembly 76 was mounted at different orientations about the longitudinal axis of the assembly 76 to test the durability of the cuff 72 under stress from various directions. The electrical continuity of the conducting band within the cuff 72 was continuously monitored by a data acquisition system.

The cuff with continuous strips failed, i.e. electrical continuity was disrupted, after an average of 143,667 cycles at 30% compression, and after 16,000 cycles at 50% compression. In contrast, the cuff with segmented strips failed, in two cases, after 5,500,000 and 3,590,000 cycles at 50% compression, and in another case after ~4,600,000 cycles including 1.40 million cycles at 30% compression and 3.18 million cycles at 50% compression. In other cases, testing terminated without failure after several million cycles at 50% compression. Consider Table 1, below:

Item Number Cuff Type Compression Ratio Cycles to Failure 1 Continuous 30% 138,000 2 Continuous 30% 63,000 3 Continuous 30% 230,000 4 Continuous 50% 16,000 5 Segmented 30% for 1.40M 4,600,000 50% for 3.18M 6 Segmented 50% 5,500,000 7 Segmented 30% for 1.19M>5,100,000* 50% for 3.68M 8 Segmented 50%>3,400,000* 9 Segmented 50%>3,400,000* 10 Segmented 50%>3,700,000* 11 Segmented 50%>3,700,000* 12 Segmented 50% 3,590,000 13 Segmented 50%>4,030,000* 14 Segmented 50%>4,030,000* *Test terminated before failure These testing data demonstrated that the cuff with segmented strips is at least twenty-five times more durable than the cuff with continuous strips. Cuffs with continuous strips, currently used in clinical practice, typically show breakage in clinical applications as early as six months after implantation. Patients thus must regularly seek further professional care to replace damaged cuffs. Thus, the disclosed cuff with segmented strips significantly increases the useful life of devices into which it is incorporated, thereby decreasing the procedures, cost, and inconvenience to patients having such implanted devices.

In one embodiment, the curled configuration of the apparatus had a diameter of 10 mm with a 1.5 wrap, meaning that one half of the circumference contained a single sandwiched sheet (i.e., 2 layers) of non-conductive material 53, and the other 1.5 wrap of the circumference contained two sandwiched sheets (i.e., 4 layers) of non-conductive material 53. Any wrap resulting in a compliant, flexible cuff that does not damage the nerve may be used. The interpolar distance was about 0.75 times to 1.5 times the inner cuff diameter. The contact surface area was relatively larger than the contact surface area of conventional electrodes, such as the electrode Naples disclosed for nerve stimulation and activation, safely delivered the required higher amount of charge to block the nerve action potential, even in nerves up to 12 mm in diameter.

In one embodiment, the electrode was bipolar. In another embodiment, the electrode used three contact groups, i.e., tripolar. In this embodiment, the electrode contained three continuous strips of conductive material, connected by electrically conductive leads (A, B, C in FIGS. 7A, 7B), that was provided between the two opposing non-conductive surfaces in the same manner as described above for two continuous strips of conductive material. The separation, i.e., distance, between the two, three, or more conductor bands is a function of the diameter of the cuff. The ratio of separation: diameter ranged between 0.75:1.5.

As mentioned above, any of the nerve cuffs described herein may include one or more tie regions or securements to secure the nerve cuff to the nerve using tie (e.g., suture, etc.). A tie may be a suture, wire, elastic, fiber, etc. For example, a tie may be a bioabsorbable suture. The tie regions may include one or more holes, channels, ridges, etc., in which the tie may reset. In general, the nerve cuff may be secured by one or more ties, within one or more tie securements. The tie may be attached in the securements (tie regions) loosely and/or elastically, to allow the nerve cuff to wrap around the nerve in a manner that allows the nerve cuff to expand and/or contract, to a limited degree (e.g., up to 5%, 10%, 15%, etc.).

Figure 12A:
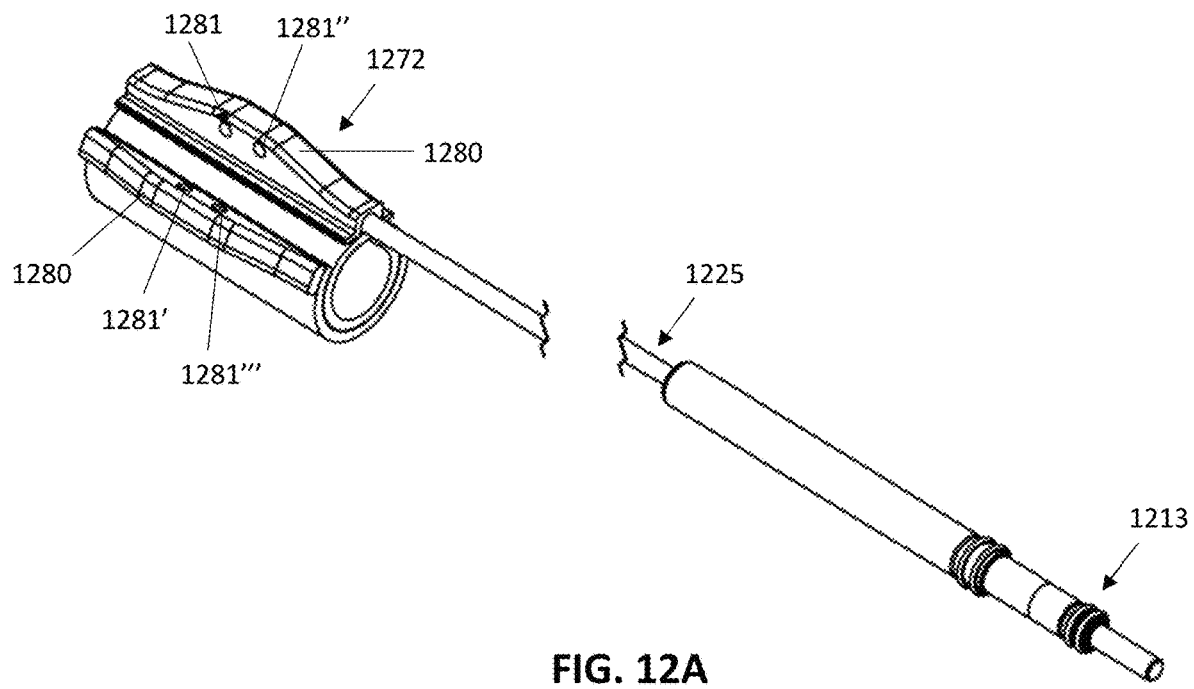
FIG. 12A illustrates one example of a nerve cuff (including a lead and lead connector) configured to be used as described herein. This variation also include a pair of tie regions that may be secured via a tie.

For example, FIG. 12A shows one example of a nerve cuff 1272 including a plurality of conductive nerve contact segments having an inner surface configured to contact a nerve trunk and an outer surface that does not contact the nerve trunk. The nerve cuff may include at least a single wire of a conductive biocompatible material operatively connecting the plurality of conductive nerve contact segments thus forming a segmented strip (which may be arranged along an inner surface of the nerve cuff). The wire may be configured as helical portions separated by non-helical portions where the non-helical portions are secured to the surface of the conductive nerve contact segments not contacting the nerve trunk, as described above. The nerve cuff may also include a conductive lead 1225 capable of operatively connecting the nerve cuff to a waveform generator (e.g., via a connector 1213) so that energy may be applied to the plurality of nerve contact segments.

Figure 12B:
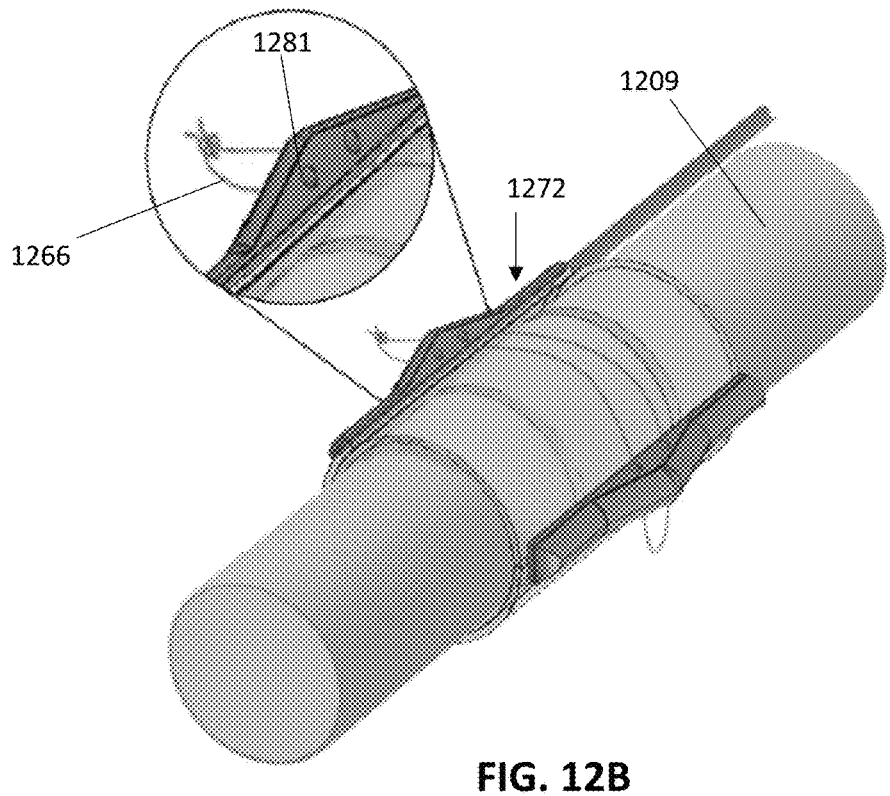
FIG. 12B schematically illustrates the attachment of a nerve cuff such as the one shown in FIG. 12A on a nerve.

In FIG. 12A the nerve cuff also includes a pair of tie securements 1280, 1280', forming two ridges that include four openings or channels 1281, 1281', 1281", 1281''' into which one or more ties may be attached. The two ridges forming the tie securements may be pulled closer together by the tie, and may be formed in the outer surface of the nerve cuff to provide attachment to a tie (not shown). In FIG. 12B, the nerve cuff 1272 is shown attached to a nerve 1209, with a tie 1266 passing through and secured to the tie securement region 1272 (in this example, the tie is a suture that passes through pairs of openings 1281 in the tie securement 1272). The tis may be secured loosely, so that the nerve cuff may be expanded slightly if or as the tissue expands. Expansion of the nerve may occur shortly after attaching the nerve cuff to the nerve, as the nerve and/or surrounding tissue may swell, e.g., up to about 10% of the dimeter at the time of insertion. Thus, the tie may be configured to be secured while allowing expansion of the diameter of the nerve cuff up to 10% (e.g., in some variations up to 12%, up to 15%, etc.).

In FIG. 12B, the tie may be a single suture that may pass through all four anchor holes of the two tie securements. For example, the tie may be a continuous loop of suture that is formed by running through the adjacent holes, as shown. As mentioned, the tie is configured to remain loose; the cuff electrode may be self-sizing and the suture (tie) may prevent unexpected and/or undesirable unwrapping of the nerve cuff from the outer surface of the nerve. Loose sutures may allow the nerve cuff to expand with swelling, as mentioned, and/or may otherwise help prevent compression of the nerve.

The above-described electrode blocked numerous nerve fascicles and/or nerve fibers. The blockage was reversible; the cuff was implantable along any length of nerve at any site, and electrical parameters (current, voltage, duration, etc.) were selected by the operator. In one embodiment, the recipient of the implantable apparatus is the operator. In one embodiment, a health care professional is the operator. Use of the electrode results in lower resistance at the interface between the nerve and the electrode. Such multiple points of contact, and relatively large openings, enables the electrode to block at least one portion of the nerve trunk. In the embodiment with a tripolar configuration, the electrode can be used to first block at least one portion of the nerve trunk, and then stimulate the other portion to verify blockage.

The inventive method has use in a variety of pain and non-pain applications. One embodiment uses the method and electrode to block peripheral nerve pain. Besides use to ameliorate amputation pain, the uses and description of which was previously described, other examples of ameliorating pain include, but are not limited to, ameliorating neuropathic pain, nociceptive pain, chronic neurogenic pain, migraine pain, post-herpetic neuralgia, pelvic pain, chronic post-surgical pain, post-surgical pain, and neuralgia. As known in the art, pain is defined as an unpleasant sensation caused by noxious stimulation of the sensory nerve endings. Amputation pain is pain resulting from the surgical removal of a part of the body or a limb or a part of a limb to treat for therapy resulting from, e.g., pathology, trauma, etc. Neuropathic pain is pain that results from the direct inputs of nervous tissue of the peripheral or central nervous system, generally felt as burning or tingling and often occurring in an area of sensory loss. Nociceptive pain is pain that results from stimulation of the neural receptors for painful stimuli, i.e., inputs of nociceptors. Chronic neurogenic pain is pain that originates in the nervous system and persists over time (i.e., not acute but chronic). Migraine pain result in headaches and is related to dilation of extracranial blood vessels, the origin of which may be defined (e.g., consumption of certain foods, external stimuli) or may be unknown. Post-herpetic neuralgia is a form of neuralgia with intractable pain that develops at the site of a previous eruption of herpes zoster. Pelvic pain is pain that is centered in the pelvis region i.e. lower part of the trunk of the body. Chronic post-surgical pain is pain persisting for a long period of time beginning after treatment of disease or trauma by manipulative and operative methods. Post-surgical pain is pain beginning after treatment of disease or trauma by manipulative and operative methods. Neuralgia is pain, often severe and characterized as "stabbing", resulting from any number of nervous system pathologies or disorders.

In other embodiments, the inventive method is used in non-pain applications where blocking the action potential of a nerve provides the desired amelioration outcome. One example of such a non-pain use is in ameliorating obesity. As known in the art, obesity is an abnormal increase in the proportion of fat cells, mainly in the viscera and subcutaneous tissues. The inventive method may be used on the vagus nerve in this embodiment. Another example of such a non-pain use in ameliorating overactive bladder, which is a colloquial term for bladder storage function disorders or pathologies. The method and electrode can be used on the pelvic nerve to ameliorate the sudden urge to void that may be difficult to suppress and may lead to incontinence. Another example of such a non-pain use is in ameliorating spasticity of any motor nerve; spasticity results in excessive muscle contraction and can be due to any of several nervous system disorders. The following hypothetical examples illustrate these embodiments.

A patient with advanced type 2 diabetes is experiencing neuropathic pain in his feet as a result of loss of blood flow to his legs. Normal doses of pain-killing narcotics are either ineffective or cause undesirable side effects. After implantation of the electrode and placement of the cuff on the right sciatic nerve trunk at the popliteal fossa, the patient self-treats pain for 10 minutes at 10 mApp, experiencing immediate pain relief. The patient repeats the procedure on demand, as needed.

A migraine patient experiences severe headaches unresponsive to conventional treatment. After implantation of the electrode and placement of the cuff on the greater occipital nerve trunk, the patient self-treats pain for 10 minutes at 10 mApp, experiencing immediate pain relief. The patient repeats the procedure on demand, as needed.

A patient with shingles experiences postherpetic neuralgia, unresponsive to conventional treatment. After implantation of the electrode and placement of the cuff on the intercostal nerves, the patient self-treats pain for 10 minutes at 10 mApp, experiencing immediate pain relief. The patient repeats the procedure on demand, as needed.

A post-operative inguinal hernia repair patient experiences chronic pain. After implantation of the electrode and placement of the cuff on the ilioinguinal nerve, the patient self-treats pain for 10 minutes at 10 mApp, experiencing immediate pain relief. The patient repeats the procedure on demand, as needed.

A patient with overactive bladder syndrome undergoes a procedure for implantation of the electrode and placement of the cuff on the pelvic nerve. The patient self-treats at 10 mApp upon an urge to urinate, experiencing urge cessation.

A patient with muscle spasticity undergoes a procedure for implantation of the electrode and placement of the cuff on a motor nerve. The patient self-treats at 10 mApp when needed, ameliorating spasticity of the muscle which the nerve innervates.

The embodiments shown and described are specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for reversibly blocking an action potential in a sensory nerve of a patient, the method comprising:
    attaching a nerve cuff electrode to a nerve trunk, where an inner surface of a plurality of conductive contact segments of the nerve cuff electrode contacts the nerve trunk, and an outer surface of the plurality of conductive contact segments do not contact the nerve trunk, wherein at least a single wire of a conductive biocompatible material is operatively connecting the plurality of conductive contact segments thus forming a segmented strip; and
    securing a tie to hold the nerve cuff electrode over the nerve trunk, wherein the tie engages with a plurality of tie securements on an outer surface of the nerve cuff electrode, and wherein the tie allows the nerve cuff electrode to expand over the nerve trunk.

2. The method of claim 1, wherein the tie limits expansion of the nerve cuff electrode to a diameter of less than 15% of a diameter of the nerve trunk.

3. The method of claim 1, wherein the nerve cuff electrode comprises a self-curling sheet of non-conductive material that is pre-tensioned to hold the plurality of conductive contact segments against the nerve trunk.

4. The method of claim 1, wherein securing the tie comprises passing the tie through openings of the nerve cuff electrode.

5. The method of claim 4, wherein the openings are within two ridges on the outer surface of the nerve cuff electrode, the method further comprising pulling the tie to bring the two ridges closer together.

6. The method of claim 1, wherein the tie is secured to the nerve cuff electrode loosely and/or elastically so that the nerve cuff electrode may expand as the nerve trunk and/or surrounding tissue expands.

7. The method of claim 1, further comprising applying a waveform frequency to the nerve cuff electrode to block conduction of the action potential.

8. The method of claim 7, wherein the waveform frequency is at least 5 kHz up to 50 kHz.

9. The method of claim 7, wherein the waveform frequency does not simulate the sensory nerve of the patient.

10. The method of claim 7, wherein applying the waveform frequency comprises applying a voltage ranging from 4 Vpp to 20 Vpp, or a current ranging from 4 mApp to 26 mApp, at the outer surface of the plurality of conductive contact segments.

11. The method of claim 1, wherein the at least the single wire is embedded in a silicone sheet.

12. The method of claim 1, wherein the nerve trunk has a diameter exceeding 3 mm and up to 12 mm.

13. The method of claim 1, wherein the tie is a suture that is configured to dissolve within the patient's body.

14. A nerve cuff electrode configured to reversibly block an action potential in a sensory nerve of a patient, the nerve cuff electrode comprising:
    a plurality of conductive contact segments having an inner surface configured to contact a nerve trunk and an outer surface configured not to contact the nerve trunk;

at least a single wire of a conductive biocompatible material operatively connecting the plurality of conductive contact segments thus forming a segmented strip;
a plurality of tie securements on an outer surface of the nerve cuff electrode, the plurality of tie securements configured to engage with a tie to secure the nerve cuff electrode to the nerve trunk; and
a conductive lead that is configured to operatively connect to a waveform generator for applying energy to the conductive contact segments.

15. The nerve cuff electrode of claim 14, wherein the tie securements include a plurality of openings on the outer surface of the nerve cuff electrode.

16. The nerve cuff electrode of claim 14, wherein the tie securements include ridges along the outer surface of the nerve cuff electrode.

17. The nerve cuff electrode of claim 14, wherein the nerve cuff electrode is configured to expand in diameter to accommodate expansion of the nerve trunk therein.

18. The nerve cuff electrode of claim 14, wherein the nerve cuff electrode is configured to apply a waveform frequency of at least 5 kHz up to 50 kHz.

19. A method for reversibly blocking an action potential in a sensory nerve of a patient, the method comprising:
attaching a nerve cuff electrode to a nerve trunk, where an inner surface of a plurality of conductive contact segments of the nerve cuff electrode contacts the nerve trunk, and an outer surface of the plurality of conductive contact segments do not contact the nerve trunk, wherein at least a single wire of a conductive biocompatible material is operatively connecting the plurality of conductive contact segments thus forming a segmented strip; and
securing a tie to hold the nerve cuff electrode over the nerve trunk, wherein the tie engages with a plurality of tie securements on an outer surface of the nerve cuff electrode; and
applying a waveform frequency to the nerve cuff electrode to block conduction of the action potential.

20. A method for reversibly blocking an action potential in a sensory nerve of a patient, the method comprising:
attaching a nerve cuff electrode to a nerve trunk, wherein the nerve trunk has a diameter exceeding 3 mm and up to 12 mm, where an inner surface of a plurality of conductive contact segments of the nerve cuff electrode contacts the nerve trunk, and an outer surface of the plurality of conductive contact segments do not contact the nerve trunk, wherein at least a single wire of a conductive biocompatible material is operatively connecting the plurality of conductive contact segments thus forming a segmented strip; and
securing a tie to hold the nerve cuff electrode over the nerve trunk, wherein the tie engages with a plurality of tie securements on an outer surface of the nerve cuff electrode.

* * * * *